(12) United States Patent    (10) Patent No.:   US 12,605,554 B2

Levin et al.      (45) Date of Patent:   *Apr. 21, 2026

(54) METHODS AND APPARATUS TO STIMULATE HEART ATRIA

(71) Applicant: BackBeat Medical, LLC, New Hope, PA (US)

(72) Inventors: Howard Levin, Teaneck, NJ (US); Mark Gelfand, New York, NY (US)

(73) Assignee: BackBeat Medical, LLC, New Hope, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,877

(22) Filed: Nov. 22, 2022

(65) Prior Publication Data

US 2023/0158308 A1     May 25, 2023

Related U.S. Application Data

(60) Continuation of application No. 16/794,478, filed on Feb. 19, 2020, now Pat. No. 11,529,520, which is a (Continued)

(51) Int. Cl.
| | |
|---|---|
| *A61N 1/362* | (2006.01) |
| *A61B 5/349* | (2021.01) |

(Continued)

(52) U.S. Cl.
CPC ............ *A61N 1/3627* (2013.01); *A61B 5/349* (2021.01); *A61N 1/3624* (2013.01); *A61N 1/368* (2013.01);

(Continued)

(58) Field of Classification Search
CPC .... A61N 1/3627; A61N 1/3624; A61N 1/368; A61N 1/3684; A61N 1/37235; A61N 1/36843

See application file for complete search history.

(56) References Cited

U.S. PATENT DOCUMENTS

| | | |
|---|---|---|
| 3,683,934 A | 8/1972 | Bukowiecki et al. |
| 3,939,844 A | 2/1976 | Pequignot |

(Continued)

FOREIGN PATENT DOCUMENTS

| | | |
|---|---|---|
| AU | 2013361318 | 8/2018 |
| AU | 2014367229 | 7/2019 |

(Continued)

OTHER PUBLICATIONS

Office Action dated May 12, 2021 in Korean Patent Application No. 10-2021-7005394, and English translation thereof.

(Continued)

*Primary Examiner* — Jennifer Pitrak McDonald
*Assistant Examiner* — Jennifer L Ghand
(74) *Attorney, Agent, or Firm* — Plumsea Law Group, LLC

(57) ABSTRACT

A method and apparatus for treatment of hypertension and heart failure by increasing vagal tone and secretion of endogenous atrial hormones by excitory pacing of the heart atria. Atrial pacing is done during the ventricular refractory period resulting in atrial contraction against closed AV valves, and atrial contraction rate that is higher than the ventricular contraction rate. Pacing results in the increased atrial wall stress. An implantable device is used to monitor ECG and pace the atria in a nonphysiologic manner.

20 Claims, 5 Drawing Sheets

Related U.S. Application Data division of application No. 15/226,056, filed on Aug. 2, 2016, now Pat. No. 10,596,380, which is a continuation of application No. 13/957,499, filed on Aug. 2, 2013, now Pat. No. 9,427,586, which is a continuation of application No. 12/987,498, filed on Jan. 10, 2011, now Pat. No. 8,515,536, which is a continuation of application No. 11/861,019, filed on Sep. 25, 2007, now Pat. No. 7,869,874.

(60) Provisional application No. 60/826,847, filed on Sep. 25, 2006.

(51) Int. Cl.
   *A61N 1/368*       (2006.01)
   *A61N 1/372*       (2006.01)

(52) U.S. Cl.
   CPC ....... *A61N 1/3684* (2013.01); *A61N 1/37235* (2013.01); *A61N 1/36843* (2017.08)

(56)             References Cited

U.S. PATENT DOCUMENTS

| | | | |
|---|---|---|---|
| 4,712,555 A | | 12/1987 | Thornander et al. |
| 5,154,171 A | | 10/1992 | Chirife |
| 5,199,428 A | | 4/1993 | Obel et al. |
| 5,213,098 A | | 5/1993 | Bennett et al. |
| 5,601,613 A | | 2/1997 | Florio et al. |
| 5,800,334 A | | 9/1998 | Wilk |
| 5,928,271 A | | 7/1999 | Hess et al. |
| 5,971,911 A | | 10/1999 | Wilk |
| 6,045,531 A | | 4/2000 | Davis |
| 6,157,859 A | * | 12/2000 | Alt ..................... A61N 1/39622 |
| | | | 607/4 |
| 6,241,678 B1 | | 6/2001 | Afremov et al. |
| 6,377,852 B1 | | 4/2002 | Bornzin et al. |
| 6,507,756 B1 | * | 1/2003 | Heynen ................ A61N 1/3627 |
| | | | 607/9 |
| 6,668,195 B2 | | 12/2003 | Warman et al. |
| 6,701,187 B1 | | 3/2004 | Bornzin et al. |
| 7,096,064 B2 | | 8/2006 | Deno et al. |
| 7,155,284 B1 | | 12/2006 | Whitehurst et al. |
| 7,184,832 B2 | | 2/2007 | Deno et al. |
| 7,233,824 B2 | | 6/2007 | Kleckner et al. |
| 7,286,873 B2 | | 10/2007 | Havel et al. |
| 7,289,849 B2 | | 10/2007 | Baynham |
| 7,363,077 B1 | | 4/2008 | Min et al. |
| 7,580,747 B1 | | 8/2009 | Farazi et al. |
| 7,674,222 B2 | | 3/2010 | Nikolic et al. |
| 7,869,874 B2 | * | 1/2011 | Levin ..................... A61B 5/349 |
| | | | 607/9 |
| 7,877,144 B2 | | 1/2011 | Coles, Jr. et al. |
| 7,908,008 B2 | | 3/2011 | Ben-David et al. |
| 8,019,416 B2 | | 9/2011 | Pastore et al. |
| 8,165,674 B2 | | 4/2012 | Levin et al. |
| 8,187,160 B2 | | 5/2012 | Criscione et al. |
| 8,224,444 B2 | | 7/2012 | Ben-David et al. |
| 8,295,928 B2 | | 10/2012 | Salo et al. |
| 8,504,149 B2 | | 8/2013 | Ibbus et al. |
| 8,571,656 B2 | | 10/2013 | Stahmann et al. |
| 8,632,470 B2 | * | 1/2014 | Stahmann .......... A61B 5/02007 |
| | | | 600/483 |
| 8,805,494 B2 | | 8/2014 | Libbus et al. |
| 9,008,769 B2 | | 4/2015 | Mika et al. |
| 9,108,062 B2 | | 8/2015 | Stahmann et al. |
| 9,333,352 B2 | | 5/2016 | Mika et al. |
| 9,370,661 B2 | * | 6/2016 | Levin ..................... A61N 1/368 |
| 9,370,662 B2 | | 6/2016 | Mika et al. |
| 9,427,586 B2 | * | 8/2016 | Levin ................ A61N 1/37235 |
| 9,526,900 B2 | | 12/2016 | Mika et al. |
| 9,592,390 B2 | | 3/2017 | Stahmann et al. |
| 9,656,086 B2 | | 5/2017 | Mika et al. |
| 9,687,636 B2 | | 6/2017 | Levin et al. |
| 9,731,136 B2 | | 8/2017 | Levin et al. |
| 9,878,162 B2 | | 1/2018 | Mika et al. |
| 9,937,351 B2 | | 4/2018 | Mika et al. |
| 10,004,905 B2 | | 6/2018 | Stahmann et al. |
| 10,071,250 B2 | | 9/2018 | Mika et al. |
| 10,173,067 B2 | | 1/2019 | Shuros et al. |
| 10,252,060 B2 | | 4/2019 | Levin et al. |
| 10,252,061 B2 | | 4/2019 | Mika et al. |
| 10,342,982 B2 | | 7/2019 | Mika et al. |
| 10,369,333 B2 | | 8/2019 | Levin et al. |
| 10,441,794 B2 | | 10/2019 | Mika et al. |
| 10,485,658 B2 | | 11/2019 | Mika et al. |
| 10,596,380 B2 | * | 3/2020 | Levin ..................... A61B 5/349 |
| 10,610,689 B2 | | 4/2020 | Mika et al. |
| 10,835,751 B2 | | 11/2020 | Stahmann et al. |
| 10,967,188 B2 | | 4/2021 | Mika et al. |
| 11,083,894 B2 | | 8/2021 | Levin et al. |
| 11,097,108 B2 | | 8/2021 | Mika et al. |
| 11,389,658 B2 | | 7/2022 | Mika et al. |
| 11,426,589 B2 | | 8/2022 | Mika et al. |
| 11,452,875 B2 | | 9/2022 | Mika et al. |
| 11,529,520 B2 | * | 12/2022 | Levin ................... A61N 1/3624 |
| 11,712,567 B2 | | 8/2023 | Mika et al. |
| 11,759,639 B2 | | 9/2023 | Levin et al. |
| 11,969,598 B2 | | 4/2024 | Mika et al. |
| 11,986,661 B2 | | 5/2024 | Mika et al. |
| 12,208,271 B2 | | 1/2025 | Mika et al. |
| 12,239,839 B2 | | 3/2025 | Levin et al. |
| 12,246,180 B2 | | 3/2025 | Mika et al. |
| 12,440,653 B2 | | 10/2025 | Levin et al. |
| 12,458,805 B2 | | 11/2025 | Mika et al. |
| 2001/0031993 A1 | | 10/2001 | Salo et al. |
| 2003/0083700 A1 | * | 5/2003 | Hill ................... A61N 1/36843 |
| | | | 607/9 |
| 2004/0044361 A1 | | 3/2004 | Frazier et al. |
| 2004/0049235 A1 | | 3/2004 | Deno et al. |
| 2004/0138715 A1 | | 7/2004 | Van Groeningen et al. |
| 2004/0186523 A1 | | 9/2004 | Florio |
| 2004/0199210 A1 | | 10/2004 | Shelchuk |
| 2004/0215268 A1 | | 10/2004 | Corbucci |
| 2005/0038478 A1 | | 2/2005 | Klepfer et al. |
| 2005/0070952 A1 | | 3/2005 | Devellian |
| 2005/0075676 A1 | | 4/2005 | Deno et al. |
| 2005/0090872 A1 | | 4/2005 | Deno et al. |
| 2005/0101998 A1 | | 5/2005 | Kleckner et al. |
| 2005/0143785 A1 | | 6/2005 | Libbus |
| 2005/0149128 A1 | | 7/2005 | Heil, Jr. et al. |
| 2005/0149131 A1 | | 7/2005 | Libbus et al. |
| 2005/0149143 A1 | | 7/2005 | Libbus et al. |
| 2005/0165454 A1 | | 7/2005 | Chinchoy |
| 2005/0234543 A1 | | 10/2005 | Glaser et al. |
| 2006/0041283 A1 | | 2/2006 | Gelfand et al. |
| 2006/0173502 A1 | | 8/2006 | Baynham |
| 2006/0264980 A1 | | 11/2006 | Khairkhahan et al. |
| 2007/0073352 A1 | | 3/2007 | Euler et al. |
| 2007/0239037 A1 | | 10/2007 | Ghio et al. |
| 2007/0299475 A1 | | 12/2007 | Levin et al. |
| 2007/0299477 A1 | | 12/2007 | Kleckner et al. |
| 2008/0027488 A1 | | 1/2008 | Coles et al. |
| 2008/0077187 A1 | | 3/2008 | Levin et al. |
| 2008/0109043 A1 | | 5/2008 | Salo et al. |
| 2008/0154322 A1 | | 6/2008 | Jackson et al. |
| 2008/0275531 A1 | | 11/2008 | Bulkes et al. |
| 2008/0281368 A1 | | 11/2008 | Bulkes et al. |
| 2009/0018608 A1 | | 1/2009 | Schwartz et al. |
| 2009/0036940 A1 | | 2/2009 | Wei et al. |
| 2009/0118783 A1 | | 5/2009 | Patangay et al. |
| 2009/0143838 A1 | | 6/2009 | Libbus et al. |
| 2009/0247809 A1 | | 10/2009 | Loeb et al. |
| 2010/0094370 A1 | | 4/2010 | Levin et al. |
| 2010/0204741 A1 | | 8/2010 | Tweden et al. |
| 2010/0312301 A1 | | 12/2010 | Stahmann |
| 2011/0160787 A1 | | 6/2011 | Greenhut et al. |
| 2011/0172731 A1 | | 7/2011 | Levin et al. |
| 2011/0224749 A1 | | 9/2011 | Ben-David et al. |
| 2012/0109237 A1 | | 5/2012 | Xiao et al. |
| 2012/0158082 A1 | | 6/2012 | Katra |
| 2012/0215272 A1 | | 8/2012 | Levin et al. |
| 2012/0215275 A1 | | 8/2012 | Wenzel et al. |

(56) References Cited

U.S. PATENT DOCUMENTS

| | | | |
|---|---|---|---|
| 2014/0128934 A1 | 5/2014 | Schwartz et al. |
| 2014/0180353 A1 | 6/2014 | Mika et al. |
| 2014/0214115 A1 | 7/2014 | Greiner et al. |
| 2015/0051660 A1 | 2/2015 | Meyer |
| 2015/0094784 A1 | 4/2015 | Karst et al. |
| 2015/0258342 A1 | 9/2015 | Mika et al. |
| 2016/0129084 A1 | 5/2016 | Caggiano et al. |
| 2016/0243368 A1 | 8/2016 | Mika et al. |
| 2016/0263383 A1 | 9/2016 | Levin et al. |
| 2017/0072203 A1 | 3/2017 | Mika et al. |
| 2017/0080235 A1 | 3/2017 | Mika et al. |
| 2017/0239481 A1 | 8/2017 | Mika et al. |
| 2017/0274190 A1 | 9/2017 | Levin et al. |
| 2017/0291032 A1 | 10/2017 | Levin et al. |
| 2017/0304048 A1 | 10/2017 | Mika et al. |
| 2018/0185652 A1 | 7/2018 | Mika et al. |
| 2018/0256899 A1 | 9/2018 | Mika et al. |
| 2019/0001141 A1 | 1/2019 | Mika et al. |
| 2019/0269927 A1 | 9/2019 | Mika et al. |
| 2019/0275336 A1 | 9/2019 | Levin et al. |
| 2019/0351237 A1 | 11/2019 | Mika et al. |
| 2020/0009357 A1 | 1/2020 | Levin et al. |
| 2020/0094060 A1 | 3/2020 | Mika et al. |
| 2020/0121451 A1 | 4/2020 | Mika et al. |
| 2020/0346015 A1 | 11/2020 | Harkema et al. |
| 2021/0346702 A1 | 11/2021 | Mika et al. |
| 2022/0008725 A1 | 1/2022 | Levin et al. |
| 2023/0026613 A1 | 1/2023 | Mika et al. |
| 2023/0032051 A1 | 2/2023 | Mika et al. |
| 2023/0233817 A1 | 7/2023 | Levin et al. |
| 2023/0405336 A1 | 12/2023 | Mika et al. |
| 2024/0033517 A1 | 2/2024 | Levin et al. |
| 2024/0173553 A1 | 5/2024 | Mika et al. |
| 2024/0299752 A1 | 9/2024 | Mika et al. |
| 2024/0335668 A1 | 10/2024 | Mika et al. |
| 2025/0152941 A1 | 5/2025 | Levin et al. |
| 2025/0152945 A1 | 5/2025 | Mika et al. |

FOREIGN PATENT DOCUMENTS

| | | | |
|---|---|---|---|
| AU | 2016319787 | | 9/2021 |
| AU | 2019204758 | | 10/2021 |
| CA | 2933278 | A1 | 6/2015 |
| CA | 2933278 | C | 3/2023 |
| CA | 2996312 | C | 2/2024 |
| CN | 1446592 | A | 10/2003 |
| CN | 1662278 | A | 8/2005 |
| CN | 2897151 | Y | 5/2007 |
| CN | 101309722 | A | 11/2008 |
| CN | 101980657 | A | 2/2011 |
| CN | 102159279 | A | 8/2011 |
| CN | 102300603 | A | 12/2011 |
| CN | 102551878 | A | 7/2012 |
| CN | 103338709 | A | 10/2013 |
| CN | 106029165 | | 10/2016 |
| CN | 104968392 | B | 11/2017 |
| CN | 107715299 | A | 2/2018 |
| CN | 108025173 | A | 5/2018 |
| CN | 106029165 | B | 11/2018 |
| CN | 109364374 | A | 2/2019 |
| CN | 107715299 | B | 6/2021 |
| CN | 108025173 | B | 3/2022 |
| CN | 109364374 | B | 8/2022 |
| CN | 109219465 | B | 10/2023 |
| CN | 117282025 | A | 12/2023 |
| EP | 0532148 | | 3/1993 |
| EP | 2241348 | A2 | 10/2010 |
| EP | 2374503 | A1 | 10/2011 |
| EP | 2934669 | B1 | 6/2017 |
| EP | 3238777 | A2 | 11/2017 |
| EP | 3082949 | B1 | 11/2018 |
| EP | 3461531 | A1 | 4/2019 |
| EP | 3238777 | B1 | 10/2019 |
| EP | 3639888 | A1 | 4/2020 |
| EP | 3461531 | B1 | 10/2020 |
| EP | 3639888 | B1 | 5/2021 |
| EP | 3347090 | B1 | 11/2021 |
| EP | 3954429 | A2 | 2/2022 |
| EP | 3954429 | A3 | 5/2022 |
| EP | 3954429 | B1 | 8/2023 |
| EP | 4233800 | A2 | 8/2023 |
| ES | 2902005 | T3 | 3/2022 |
| HK | 1226016 | B2 | 10/2019 |
| HK | 1243968 | B | 12/2021 |
| IN | 202148037573 | A | 8/2021 |
| IN | 202248072569 | A | 12/2022 |
| JP | H07171218 | A | 7/1995 |
| JP | 2620819 | | 6/1997 |
| JP | 2002505172 | A | 2/2002 |
| JP | 2007-519441 | A | 7/2007 |
| JP | 2007527742 | A | 10/2007 |
| JP | 2007-531609 | A | 11/2007 |
| JP | 2010-508979 | A | 3/2010 |
| JP | 2010-509024 | | 3/2010 |
| JP | 2010-512958 | A | 4/2010 |
| JP | 2010512855 | A | 4/2010 |
| JP | 2010-536481 | A | 12/2010 |
| JP | 2010536530 | A | 12/2010 |
| JP | 2016501639 | A | 1/2016 |
| JP | 2016-540589 | A | 12/2016 |
| JP | 2019-042579 | | 3/2019 |
| JP | 6510421 | B2 | 5/2019 |
| JP | 2019-517842 | A | 6/2019 |
| JP | 2019-111408 | A | 7/2019 |
| JP | 6831087 | B2 | 2/2021 |
| JP | 2021013822 | A | 2/2021 |
| JP | 6839163 | B2 | 3/2021 |
| JP | 6999545 | | 12/2021 |
| JP | 7050693 | B2 | 3/2022 |
| JP | 2022087144 | A | 6/2022 |
| JP | 7138202 | B2 | 9/2022 |
| JP | 2022-169807 | A | 11/2022 |
| JP | 7222962 | B2 | 2/2023 |
| JP | 7395638 | B2 | 12/2023 |
| JP | 2024-037754 | A | 3/2024 |
| JP | 7672471 | B2 | 4/2025 |
| JP | 2025108698 | A | 7/2025 |
| JP | 7759859 | B | 10/2025 |
| KR | 102221586 | B1 | 3/2021 |
| KR | 102323562 | B1 | 11/2021 |
| KR | 10-2367191 | B1 | 2/2022 |
| KR | 10-2471841 | B1 | 11/2022 |
| KR | 10-2630590 | B1 | 1/2024 |
| WO | 9944680 | A1 | 9/1999 |
| WO | 2009035515 | A1 | 3/2005 |
| WO | 2005063332 | A1 | 7/2005 |
| WO | 2005097256 | A2 | 10/2005 |
| WO | 2007007058 | A1 | 1/2007 |
| WO | 2007021258 | | 2/2007 |
| WO | 2007044279 | A1 | 4/2007 |
| WO | 2008057631 | A1 | 5/2008 |
| WO | 2008063470 | A1 | 5/2008 |
| WO | 2008076853 | A2 | 6/2008 |
| WO | 2008079370 | A1 | 7/2008 |
| WO | 2014100429 | A1 | 6/2014 |
| WO | 2015094401 | A1 | 6/2015 |
| WO | 2017044794 | A1 | 3/2017 |
| WO | 2017184912 | A2 | 10/2017 |
| WO | 2023230501 | A2 | 11/2023 |
| WO | 2023235722 | A1 | 12/2023 |

OTHER PUBLICATIONS

Notice of Acceptance dated May 18, 2021 in Australian Patent Application No. 2016319787.

First Examination Report mailed May 20, 2021 in Indian Patent Application No. 201847042937.

Notice of Intention to Grant dated May 21, 2021 in European Patent Application No. 16 845 150.8.

Notice of Intention to Grant dated Jun. 2, 2021 in European Patent Application No. 17 786 669.6.

Notice of Acceptance dated Jun. 15, 2021 in Australian Patent Application No. 2019204758.

(56) References Cited

OTHER PUBLICATIONS

Response to Office Action filed Jun. 17, 2021 in Canadian Patent Application No. 2,893,222.
First Examination Report dated Jun. 18, 2021 in Australian Patent Application No. 2017252310.
Response to Office Action filed Jul. 8, 2021 in Korean Patent Application No. 10-2021-7005394, and machine English translation thereof.
Request for Trial and Amendment filed Aug. 2, 2021 in Japanese Patent Application No. 2018-512118, and machine English translation thereof.
Notice of Allowance mailed Jul. 21, 2021 in Korean Patent Application No. 10-2016-7019183, and English translation thereof.
Notice of Allowance mailed Mar. 7, 2023 in U.S. Appl. No. 17/205,114.
Second Office Action dated Apr. 11, 2023 in Chinese Patent Application No. 201780034227X, and machine English translation thereof.
Notice of Allowability mailed Apr. 27, 2023 in U.S. Appl. No. 17/205,114.
Notice of Allowance mailed May 5, 2023 in U.S. Appl. No. 17/361,774.
Notice of Allowance mailed Mar. 7, 2022 in U.S. Appl. No. 16/431,776.
Amendment filed Mar. 16, 2022 in U.S. Appl. No. 16/663,573.
Response to First Examination Report filed Apr. 6, 2022 in Indian Application No. 201847012769.
Response to Office Action filed Apr. 11, 2022 in Korean Patent Application No. 10-2021-7035610, and machine English translation thereof.
Response to Office Action filed Apr. 25, 2022 in Chinese Patent Application No. 2018113777986 and English translation thereof.
Notice of Allowance mailed Apr. 29, 2022 in U.S. Appl. No. 16/663,573.
Response to Second Examination Report filed May 4, 2022 in Australian Application No. 2017252310.
Notice of Allowance mailed May 6, 2022 in U.S. Appl. No. 16/583,371.
Notice of Allowance mailed Mar. 15, 2017 in U.S. Appl. No. 15/163,078.
Office Action mailed Mar. 24, 2017 in U.S. Appl. No. 15/372,603.
Decision to Grant issued May 26, 2017 in European Patent Application No. 13826807.3.
Office Action mailed Jun. 16, 2017 in U.S. Appl. No. 14/652,856.
Amendment filed Jun. 26, 2017 in U.S. Appl. No. 15/372,603.
Partial European Search Report issued Jul. 25, 2017 in European Patent Application No. 17169068.8.
Extended European Search Report issued Jul. 25, 2017 in European Patent Application No. 14871226.8.
PCT Invitation to Pay Additional Fees mailed Aug. 3, 2017 in International Application No. PCT/US2017/028715.
Office Action issued Aug. 11, 2017 in European Patent Application No. 14871226.8.
Notice of Allowance issued Sep. 11, 2017 in U.S. Appl. No. 15/372,603.
Amendment Filed Sep. 18, 2017 in U.S. Appl. No. 14/652,856.
Office Action mailed Sep. 21, 2017 in U.S. Appl. No. 15/628,870.
Office Action mailed Sep. 27, 2017 in U.S. Appl. No. 15/589,134.
International Search Report and Written Opinion issued Oct. 3, 2017 in International Application No. PCT/US2017/028715.
Chaliki, HP et al.; "Pulmonary Venous Pressure: Relationship to Pulmonary Artery, Pulmonary Wedge, and Left Atrial Pressure in Normal, Lightly Sedated Dogs"; Catheterization and Cardiovascular Interventions; vol. 56, Issue 3; Jun. 17, 2002; p. 432, Abstract.
Office Action issued Oct. 19, 2017 in Japanese Patent Application No. 2015-549718, and English translation thereof.
Office Action issued Nov. 6, 2017 in Australian Patent Application No. 2013361318.

Office Action mailed Nov. 21, 2017 in U.S. Appl. No. 15/259,282.
Extended European Search Report issued Nov. 3, 2017 in European Patent Application No. 17169068.8.
Amendment and Declaration Under 37 CFR 1.132 filed Jan. 22, 2018 in U.S. Appl. No. 15/628,870.
Amendment filed Jan. 26, 2018 in U.S. Appl. No. 15/589,134.
Notice of Allowance mailed Dec. 6, 2017 in U.S. Appl. No. 14/652,856.
Supplemental Notice of Allowance mailed Jan. 29, 2018 in U.S. Appl. No. 14/652,856.
Response to Office Action filed Feb. 7, 2018 in European Patent Application No. 14 871 226.8.
Response to Office Action filed Feb. 21, 2018 in U.S. Appl. No. 15/259,282.
Office Action issued Feb. 24, 2018 in Chinese Patent Application No. 201480075987.1, and English translation thereof.
Notification Concerning Transmittal of International Preliminary Report on Patentability (IPRP) dated Mar. 22, 2018 in International Application No. PCT/2016/051023.
Response to Office Action filed Mar. 28, 2018 in Japanese Patent Application No. 2015-549718, with machine English translation of Remarks and English translation of Amended Claims.
Office Action mailed Apr. 10, 2018 in U.S. Appl. No. 15/259,282.
Response to Examination Report filed Apr. 23, 2018 in Australian Patent Application No. 2013361318.
Notice of Allowance mailed May 2, 2018 in U.S. Appl. No. 15/589,134.
Notice of Acceptance issued May 7, 2018 in Australian Patent Application No. 2013361318.
Notice of Intention to Grant issued May 7, 2018 in European Patent Application No. 14871226.8.
Office Action issued May 10, 2018 in Japanese Patent Application No. 2016-539929, and English translation thereof.
Office Action mailed May 16, 2018 in U.S. Appl. No. 15/628,870.
Office Action mailed May 16, 2018 in U.S. Appl. No. 15/851,787.
Response to Extended European Search Report filed May 25, 2018 in European Patent Application No. 17 169 068.8.
Response to Office Action filed Jul. 11, 2018 in Chinese Patent Application No. 201480075987.1, and English machine translation thereof.
Amendment filed Aug. 9, 2018 in U.S. Appl. No. 15/259,282.
Office Action mailed Aug. 9, 2018 in U.S. Appl. No. 15/911,249.
Response to Office Action filed Aug. 13, 2018 in U.S. Appl. No. 15/628,870.
Amendment filed Aug. 13, 2018 in U.S. Appl. No. 15/851,787.
Final Office Action issued Aug. 28, 2018 in Japanese Patent No. 2015-549718, and English translation thereof.
Final Office Action mailed Oct. 1, 2018 in U.S. Appl. No. 15/259,282.
Response to Final Office Action Filed Oct. 24, 2018 in Japanese Patent Application No. 2015-549718, with English Translation of Amended Claims and English Machine Translation of Remarks.
Response to Office Action filed Oct. 29, 2018 in Japanese Patent Application No. 2016-539929, with English Translation of Amended Claims and English Machine Translation of Remarks.
Notice of Allowance mailed Oct. 31, 2018 in U.S. Appl. No. 15/851,787.
Restriction Requirement mailed Nov. 1, 2018 in U.S. Appl. No. 15/492,802.
Notification Concerning Transmittal of International Preliminary Report on Patentability (IPRP) dated Nov. 1, 2018 in International Application No. PCT/2017/028715.
Notice of Allowance dated Sep. 7, 2023 in Canadian Patent Application No. 2,996,312.
Office Action mailed Sep. 25, 2023 in U.S. Appl. No. 17/882,811.
Office Action dated Oct. 3, 2023 in Canadian Patent Application No. 3,147,251.
Decision to Grant a Patent dated Oct. 5, 2023 in Japanese Patent No. 2022-054216, and English translation thereof.
Extended European Search Report dated Oct. 6, 2023 in European Patent Application No. 23181110.0.
Notice of Allowance mailed Oct. 30, 2023 in Korean Patent Application No. 10-2018-7010005, and English machine translation thereof.

(56) References Cited

OTHER PUBLICATIONS

International Search Report and Written Opinion for Application No. PCT/US2023/067649, mailed on Nov. 6, 2023.
Response to Office Action filed Nov. 13, 2023 in Japanese Patent Application No. 2022-140686, with English Translation of Amended Claims and English Machine Translation of Remarks.
International Search Report and Written Opinion for Application No. PCT/US2023/067392, mailed on Nov. 16, 2023.
Response to Office Action filed Dec. 4, 2023 in U.S. Appl. No. 17/883,905.
Response to Office Action filed Aug. 12, 2021 in Chinese Patent Application No. 2016800526048, and English translation thereof.
Response to First Examination Report filed Aug. 19, 2021 in Indian Patent Application No. 4286/CHENP/2015.
Second Office Action dated Aug. 26, 2021 in Chinese Patent Application No. 2016800526048, and machine English translation thereof.
Office Action mailed Sep. 7, 2021 in U.S. Appl. No. 16/431,776.
Second Office Action dated Sep. 9, 2021 in Canadian Patent Application No. 2,933,278.
Office Action mailed Sep. 15, 2021 in U.S. Appl. No. 16/583,371.
Notice of Allowance dated Sep. 24, 2021 in Canadian Patent Application No. 2,893,222.
Response to Office Action filed Sep. 28, 2021 in Japanese Patent Application No. 2018-554557, and machine English translation thereof.
Office Action dated Sep. 30, 2021 in Japanese Patent Application No. 2020-189356, and English translation thereof.
Decision to Grant dated Oct. 7, 2021 in European Patent Application No. 16 845 150.8.
First Examination Report dated Oct. 8, 2021 in Indian Patent Application No. 201847012769.
Decision to Grant dated Oct. 21, 2021 in European Patent Application No. 17 786 669.6.
Notice of Allowance mailed Nov. 25, 2020 in Korean Patent Application No. 10-2015-7019640, and English translation thereof.
Response to Office Action dated Dec. 10, 2020 in European Patent Application No. 16845150.8.
Final Office Action dated Dec. 14, 2020 in U.S. Appl. No. 16/359,218.
Response to Office Action dated Dec. 22, 2020 in Korean Patent Application No. 10-2016-7019183, and machine English translation thereof.
Examination Report dated Dec. 31, 2020 in Indian Patent Application No. 4286/CHENP/2015.
Intention to Grant dated Jan. 12, 2021 in European Patent Application No. 19 196 148.1.
Decision to Grant a Patent dated Jan. 14, 2021 in Japanese Patent No. 2018-238255, and English translation thereof.
Response Second Office Action dated Jan. 25, 2021 in Canadian Patent Application No. 2893222.
Response to Second Office Action dated Jan. 27, 2021 in Chinese Patent Application No. 2017109301826, and English translation thereof.
Response to Office Action filed Feb. 11, 2021 in U.S. Appl. No. 16/840,673.
Response to Final Office Action filed Aug. 8, 2022 in Japanese Patent Application No. 2020189356,machine English translation thereof and English translation of claims.
Notice of Allowability mailed Aug. 17, 2022 in U.S. Appl. No. 16/583,371.
Notice of Allowance mailed Aug. 29, 2022 in Korean Patent Application No. 10-2021-7035610,translation thereof.
Notice of Allowance dated Aug. 30, 2022 in Canadian Patent Application 2,933,278.
Amendment filed Sep. 12, 2022 in U.S. Appl. No. 16/453,311.
Notice of Allowance mailed Oct. 6, 2022 in U.S. Appl. No. 16/453,311.
Office Action dated Oct. 11, 2022 in Canadian Patent Application No. 2,996,312.

Certificate of Grant dated Oct. 20, 2022 in Australian Patent Application No. 2017252310.
Intimation of Grant and Patent Certificate dated Oct. 26, 2022 in Indian Patent Application No. 201847042937.
Response to EPO Communication dated Oct. 27, 2022 in European Patent Application No. 21201099.5.
Notice of Acceptance mailed Jun. 5, 2020 in Australian Patent Application No. 2018217270.
Office Action dated Jun. 9, 2020 in Chinese Patent Application No. 2017109301826, and English machine translation thereof.
First Examination Report dated Jun. 22, 2020 in Australian Patent Application No. 2019204758.
Office Action dated Jun. 23, 2020 in U.S. Appl. No. 16/276,958.
Response to Office Action filed Jul. 10, 2020 in Korean Patent Application No. 10-2015-7019640, and English machine translation thereof.
Office Action dated Jul. 30, 2020 in Japanese Patent No. 2018-238255, and English translation thereof.
Office Action dated Jul. 30, 2020 in Japanese Patent Number 2018-512118, and English translation thereof.
Notice of Allowance dated Mar. 3, 2021 in Chinese Patent Application No. 2017109301826, with machine English translation thereof.
Office Action dated Mar. 29, 2021 in Chinese Patent Application No. 2016800526048, with machine English translation thereof.
Office Action dated Apr. 1, 2021 in Japanese Patent Application No. 2018-554557, with English translation thereof.
Decision of Refusal dated Apr. 8, 2021 in Japanese Patent Application No. 2018-512118, with English translation thereof.
Decision to Grant dated Apr. 15, 2021 in European Patent Application No. 19196148.1.
Response After Final Rejection filed Feb. 24, 2021 in U.S. Appl. No. 16/359,218.
Response to Office Action dated Mar. 5, 2021 in Canadian Patent Application No. 2933278.
Response to Second Office Action dated Mar. 11, 2021 in European Patent Application No. 17 786 669.6.
Notice of Allowance dated Mar. 29, 2021 in U.S. Appl. No. 16/359,218.
Notice of Allowance mailed Apr. 21, 2021 in U.S. Appl. No. 16/840,673.
Response to Examiner's report filed May 7, 2021 in Australian Patent Application No. 2016319787.
Decision to Grant mailed Mar. 3, 2022 in Japanese Patent Application No. JP2018-554557, and English translation thereof.
First Examination Report mailed Mar. 17, 2022 in Indian Patent Application No. 202148037573.
Extended European Search Report dated Apr. 7, 2022 in European Patent Application No. 21201099.5.
Hearing Notice mailed Apr. 26, 2022 in Indian Patent Application No. 4286/CHENP/2015.
Lopez et al., "Reducing Heart Rate of the Dog by Electrical Stimulation", pp. 414-429, vol. 15 (Circ. Res. 1964).
Lister et al., "The Hemodynamic Effect of Slowing the Heart Rate by Paired or Coupled Stimulation of the Atria", pp. 362-368 (Am. Heart J. Mar. 1967).
Braunwald et al., "Editorial: Paired Electrical Stimulation of the Heart: A Physiologic Riddle and a Clinical Challenge," pp. 677-681, vol. 32, No. 5 (Circulation Nov. 1965).
Arbel et al., "Successful Treatment of Drug-Resistant Atrial Tachycardia and Intractable Congestive Heart Failure with Permanent Coupled Atrial Pacing," pp. 366-340, vol. 41 (Am. J. of Cardiology Feb. 1978).
"Information Manual, Model 5837 R-Wave Coupled Pulse Generator", 20 pages, Prelim. Ed. III, Medtronic (Jul. 1965).
Siddons et al., Cardiac Pacemakers, pp. 200-217, Pub. No. 680 of American Lecture Series (1968, Charles Thomas Publisher).
Schoonderwoerd, Bas A., "Atrial Natriuretic Peptides During Experimental Atrial Tachycardia: Role of Developing Tachycardiomyopathy", Journal of Cardiovascular Electrophysiology, vol. 15, No. 8, Aug. 2004, pp. 927-932.

(56) References Cited

OTHER PUBLICATIONS

Nishimura, Kazunobu et al., "Atrial pacing stimulates secretion of atrial natriuretic polypeptide without elevation of atrial pressure in awake dogs with experimental complete atrioventricular block." Circ. Res. 1990;66;115-122.

Willems, Rik M.D. et al., "Different Patterns of Angiotensin II and Atrial Natriuretic Peptide Secretion in a Sheep Model of Atrial Fibrillation." Journal of Cardiovascular Electrophysiology. 2001;12. 12;1387-1392.

Zupan, Igor et al., "Effects of Systolic Atrial Function on Plasma Renin Activity and Natriuretic Peptide Secretion after High Rate Atrial and Ventricular Pacing in Dogs." Pace. 2005;28.Supp 1;S270-S274.

Calderone, Angelino "The Therapeutic Effect of Natriuretic Peptides in Heart Failure; Differential Regulation of Endothelial and Inducible Nitric Oxide Synthases" Heart Failure Reviews, 2003;8;55-70.

Han, Bo et al., "Cardiovascular Effects of Natriuretic Peptides and Their Interrelation with Endothelin-1" Cardiovascular Drugs and Therapy, 2003;17;41-52.

PCT Invitation to Pay Additional Fees mailed Oct. 17, 2014 in International Application No. PCT/US2014/042777.

PCT Notification of Transmittal of the International Search Report and the Written Opinion of the International Searching Authority; International Search Report; and Written Opinion, mailed Jan. 2, 2015 in International Application No. PCT/US2014/042777.

PCT Notification of Transmittal of the International Search Report and the Written Opinion of the International Searching Authority; Declaration of Non-Establishment of International Search Report; and PCT Written Opinion of International Searching Authority, mailed Apr. 24, 2014 in International Application No. PCT/US2013/076600.

Notice of Allowance mailed Dec. 16, 2014 in U.S. Appl. No. 13/826,215.

Office Action mailed Jan. 29, 2015 in U.S. Appl. No. 13/688,978.

Amendment filed May 26, 2015 in U.S. U.S. Appl. No. 13/688,978.

Office Action mailed Jun. 10, 2015 in U.S. Appl. No. 13/960,015.

Amendment filed Dec. 3, 2015 in U.S. Appl. No. 13/960,015.

Office Action mailed Jul. 13, 2015 in U.S. Appl. No. 14/642,952.

Amendment filed Oct. 9, 2015 in U.S. Appl. No. 14/642,952.

Office Action mailed Aug. 14, 2015 in U.S. Appl. No. 13/688,978.

Amendment filed Nov. 5, 2015 in U.S. Appl. No. 13/688,978.

Office Action mailed Nov. 4, 2015 in U.S. Appl. No. 14/427,478.

Notice of Allowance mailed Jan. 8, 2016 in U.S. Appl. No. 14/642,952.

Amendment filed Jan. 13, 2016 in U.S. Appl. No. 14/427,478.

Final Office Action mailed Jan. 20, 2016 in U.S. Appl. No. 13/960,015.

Notice of Allowance mailed Feb. 12, 2016 in U.S. Appl. No. 13/688,978.

Notice of Allowance mailed Feb. 12, 2016 in U.S. Appl. No. 14/427,478.

Office Action mailed Mar. 4, 2016 in U.S. Appl. No. 14/667,931.

Amendment filed Apr. 7, 2016 in U.S. Appl. No. 13/960,015.

Advisory Action mailed Apr. 18, 2016 in U.S. Appl. No. 13/960,015.

Office Action issued May 27, 2016 in European Patent Application No. 13826807.3.

Amendment filed Jun. 6, 2016 in U.S. Appl. No. 13/960,015.

Office Action mailed Jun. 28, 2016 in U.S. Appl. No. 15/143,742.

Office Action mailed Jul. 21, 2016 in U.S. Appl. No. 13/960,015.

Amendment filed Jul. 25, 2016 in U.S. Appl. No. 14/667,931.

Office Action mailed Jul. 27, 2016 in U.S. Appl. No. 15/163,078.

Notice of Allowance mailed Aug. 17, 2016 in U.S. Appl. No. 14/667,931.

Office Action issued Sep. 5, 2016 in Chinese Patent Application No. 201380072479.3, and English translation thereof.

Amendment filed Sep. 27, 2016 in U.S. Appl. No. 15/143,742.

Response to Office Action filed Sep. 27, 2016 in European Patent Application No. 13826807.3.

Amendment filed Oct. 26, 2016 in U.S. Appl. No. 15/163,078.

PCT Notification of Transmittal of the International Search Report and the Written Opinion of the International Searching Authority;

International Search Report; and Written Opinion, mailed Nov. 28, 2016 in International Application No. PCT/US2016/051023.

Notice of Intention to Grant issued Jan. 3, 2017 in European Patent Application No. 13826807.3.

Notice of Allowance mailed Jan. 18, 2017 in U.S. Appl. No. 15/143,742.

Amendment filed Jan. 19, 2017 in U.S. Appl. No. 13/960,015.

Response to Office Action filed Jan. 19, 2017 in Chinese Patent Application No. 201380072479.3, and English translation thereof.

Notice of Allowance mailed Feb. 22, 2017 in U.S. Appl. No. 13/960,015.

Response to Office Action dated Feb. 9, 2023 in Canadian Patent Application No. 2996312.

Notice of Intention to Grant dated Feb. 21, 2023 in European Patent Application No. 21201099.5.

Response to Office Action dated Mar. 3, 2023 in Chinese Patent Application No. 201780034227X, and English Translation thereof.

First Examination Report dated Mar. 10, 2023 in Indian Patent Application No. 202248072569.

Office Action dated Mar. 6, 2023 in Canadian Patent Application No. 3021336.

Office Action dated Mar. 30, 2023 in Japanese Patent Application No. 2022-054216, with English translation thereof.

Office Action dated Apr. 10, 2023 in Korean Patent Application No. 10-2018-7010005, and machine English translation thereof.

Response to the First Examination Report filed Feb. 8, 2022 in Indian Patent Application No. 201847042937.

Second Examination Report dated Feb. 8, 2022 in Australian Patent Application No. 2017252310.

First Office Action dated Feb. 10, 2022 in Korean Patent Application No. 10-2021-7035610, and machine English translation thereof.

Response to First Office Action filed Feb. 18, 2022 in Japanese Patent Application No. JP2021-002191, with machine English translation thereof and English translation of claims.

Decision to Grant a Patent issued Dec. 6, 2018 in Japanese Patent Application No. 2016-539929, with English translation thereof.

First Examination Report Dated Dec. 12, 2018 in Australian Patent Application No. 2014367229.

Extended European Search Report issued Jan. 21, 2019 in European Patent Application No. 18205392.6.

Decision to Grant a Patent issued Mar. 1, 2019 in Japanese Patent Application No. 2015-549718, and English translation thereof.

Notice of Acceptance issued Mar. 22, 2019 in Australian Patent Application No. 2014367229.

Extended European Search Report issued Mar. 27, 2019 in European Patent Application No. 16845150.8.

Amendment After Final Rejection filed Feb. 1, 2019 in U.S. Appl. No. 15/259,282.

Response to Examination Report filed Feb. 22, 2019 in Australian Patent Application No. 2014367229.

Notice of Allowance mailed Mar. 1, 2019 in U.S. Appl. No. 15/259,282.

Office Action mailed Mar. 18, 2019 in U.S. Appl. No. 15/492,802.

Notice of Allowance mailed Mar. 19, 2019 in U.S. Appl. No. 15/613,344.

Response to Office Action filed Mar. 27, 2019 in U.S. Appl. No. 16/124,283.

Office Action mailed Apr. 8, 2019 in U.S. Appl. No. 15/911,249.

Notice of Allowance mailed Jun. 5, 2019 in U.S. Appl. No. 16/124,283.

Amendment filed Jun. 14, 2019 in U.S. Appl. No. 15/492,802.

Notice of Allowance mailed Jul. 2, 2019 in U.S. Appl. No. 15/492,802.

Amendment filed Jul. 8, 2019 in U.S. Appl. No. 15/911,249.

Notice of Intention to Grant issued May 10, 2019 in European Patent Application No. 17169068.8.

Final Office Action mailed Aug. 30, 2019 in U.S. Appl. No. 15/911,249.

Response to Office Action filed Sep. 9, 2019 and Sep. 18, 2019 in European Patent Application No. 18205392.6.

Response to First Examination Report filed Sep. 27, 2019 in Australian Patent Application No. 2018217270.

Response to Office Action filed Oct. 9, 2019 in European Patent Application No. 16845150.8.

(56)     References Cited

OTHER PUBLICATIONS

Response to Final Office Action filed Oct. 30, 2019 in U.S. Appl. No. 15/911,249.
Notice of Allowance mailed Nov. 22, 2019 in U.S. Appl. No. 15/911,249.
Response to European Office Action filed Dec. 4, 2019 in European Patent Application No. 19196148.1.
Notice of Allowance issued Sep. 27, 2019 in Hong Kong Patent Application No. 16114537.3.
Second Office Action issued Oct. 14, 2019 in Australian Patent Application No. 2018217270.
European Office Action issued Nov. 15, 2019 in European Patent Application No. 19196148.1.
Extended European Search Report issued Nov. 28, 2019 in European Patent Application No. 17786669.6.
First Office Action issued Dec. 5, 2019 in Japanese Patent Application No. 2018-238255, and English translation thereof.
Notice of Allowance mailed Nov. 26, 2018 in U.S. Appl. No. 15/628,870.
Interview Summary mailed Dec. 12, 2018 in U.S. Appl. No. 15/911,249.
Response to Restriction Requirement filed Dec. 19, 2018 in U.S. Appl. No. 15/492,802.
Office Action mailed Dec. 27, 2018 in U.S. Appl. No. 16/124,283.
Amendment filed Jan. 9, 2019 in U.S. Appl. No. 15/911,249.
Interview Summary mailed Jan. 22, 2019 in U.S. Appl. No. 15/259,282.
Canadian Office Action issued Feb. 4, 2020 in Canadian Patent Application No. 2,893,222.
First Examination Report issued Jun. 25, 2019 in Australian Patent Application No. 2018217270.
Office Action dated Feb. 4, 2020 in Canada Patent Application No. 2893222.
Extended European Search Report dated Mar. 25, 2020 in European Patent Application No. 19196148.1.
Notice of Intention to Grant dated Mar. 26, 2020 in European Patent Application No. 18205392.6.
Office Action dated Apr. 28, 2020 in European Patent Application No. 19196148.1.
Response to Office Action filed May 5, 2020 in Canada Patent Application Number 2893222.
Office Action dated May 7, 2020 in Japanese Patent No. 2019-072248, and English translation thereof.
Response to Office Action filed May 12, 2020 in Japanese Patent Application No. 2018-238255, and English translation thereof.
Office Action dated May 15, 2020 in Korean Patent No. 10-2015-7019640, and English translation thereof.
Office Action dated May 19, 2020 in Australian Patent Number 2016319787.
Response to Office Action filed Jun. 3, 2020 in European Patent Application Number 17786669.6.
Office Action dated June 4, 2020 in European Patent Application No. 16845150.8.
Office Action mailed Jun. 8, 2020 in U.S. Appl. No. 16/359,218.
Response to Office Action filed Jun. 19, 2020 Japanese Patent No. 2019-072248, and English translation thereof.
Office Action dated Oct. 19, 2022 in Chinese Patent Application No. 201780034227X, and English translation thereof.
Corrected Notice of Allowability dated Nov. 16, 2022 in U.S. Appl. No. 16/453,311.
Office Action mailed Nov. 22, 2022 in U.S. Appl. No. 17/205,114.
Notice of Decision to Grant a Patent dated Dec. 8, 2022 in Japanese Patent Application No. 2020-189356, and English translation thereof.
Response to First Examination Report filed Dec. 15, 2022 in Indian Patent Application No. 202148037573.
Response to First Examination Report filed Dec. 26, 2022 in Indian Patent Application No. 202248006588.
Corrected Notice of Allowability dated Jan. 12, 2023 in U.S. Appl. No. 16/453,311.

Office Action mailed Jan. 19, 2023 in U.S. Appl. No. 17/361,774.
Office Action dated May 10, 2022 in European Patent Application No. 21201099.5.
Notice of Grant dated May 11, 2022 in Chinese Patent Application No. 2018113777986, and machine English translation thereof.
Final Office Action dated May 12, 2022 in Japanese Patent Application No. 2020-189356, and English translation thereof.
Examination Report No. 3 dated Jun. 1, 2022 in Australian Patent Application No. 2017252310.
Response to 3rd Examination Report dated Jun. 10, 2022 in Australian Patent Application 2017252310.
Office Action dated Jun. 13, 2022 in U.S. Appl. No. 16/453,311.
Written Submission dated Jun. 21, 2022 in Indian Patent Application 4286/CHENP/2015.
First Examination Report dated Jun. 28, 2022 in Indian Patent Application No. 202248006588.
Notice of Acceptance for Patent Application dated Jun. 23, 2022 in Australian Patent Application 2017252310.
Notice of Decision to Grant a Patent dated Jul. 7, 2022 in Japanese Patent Application 2021-002191, and English translation thereof.
Intimation of Grant, Decision, and Patent Certificate dated Jul. 14, 2022 in Indian Patent Application 4286/CHENP/2015.
Response to First Examination Report dated Sep. 3, 2020 in Australian Patent Application No. 2019204758.
Response to First Examination Report dated Oct. 2, 2020 in Australian Patent Application No. 2016319787.
Response to Office Action dated Oct. 5, 2020 in Japanese Patent Application No. 2018-512118, and English translation thereof.
Amendment filed Oct. 8, 2020 in U.S. Appl. No. 16/359,218.
Response to Office Action dated Oct. 20, 2020 in European Patent Application No. 19 196 148.1.
Response to Office Action dated Oct. 26, 2020 in Chinese Patent Application No. 2017109301826, and English translation thereof.
Office Action mailed Nov. 12, 2020 in U.S. Appl. No. 16/840,673.
Response to Office Action dated Nov. 13, 2020 in Japanese Patent Application No. 2018-238255, and English translation thereof.
Certificate of Grant dated Oct. 1, 2020 in Australian Patent Application No. 2018217270.
Second Examination Report dated Oct. 1, 2020 in Australian Patent Application No. 2019204758.
Second Office Action dated Oct. 5, 2020 in Canadian Patent Application No. 2893222.
Office Action dated Oct. 23, 2020 in Korean Patent Application No. 10-2016-7019183, and English translation thereof.
Second Examination Report dated Oct. 26, 2020 in Australian Patent Application No. 2016319787.
Office Action dated Nov. 5, 2020 in European Patent Application No. 17786669.6.
Office Action dated Nov. 9, 2020 in Canadian Patent Application No. 2933278.
Office Action dated Nov. 13, 2020 in Chinese Patent Application No. 2017109301826, and English translation thereof.
Decision to Grant a Patent dated Nov. 26, 2020 in Japanese Patent No. 2019-072248, and English translation thereof.
Notice of Allowance mailed Nov. 19, 2020 in U.S. Appl. No. 16/276,958.
Amendment filed Sep. 22, 2020 in U.S. Appl. No. 16/276,958.
Corrected Notice of Allowability dated Jun. 14, 2023 in U.S. Appl. No. 17/205,114.
Response to Office Action filed Jun. 25, 2023 in Chinese Patent Application No. 201780034227X and English translation thereof.
Response to Office Action filed Jun. 29, 2023 in Japanese Patent Application No. 2022-054216, with machine English translation thereof.
Rectification for Response to the Second Office Action filed Jun. 29, 2023 in Chinese Patent Application No. 201780034227X and English translation thereof.
Response to Office Action filed Jul. 4, 2023 in Canadian Patent Application No. 3021336.
Decision to Grant dated Jul. 6, 2023 in European Patent Application No. 21201099.5.
Response to Office Action filed Jul. 7, 2023 in Korean Patent Application No. 10-2018-7010005, and machine English translation thereof.

(56) References Cited

OTHER PUBLICATIONS

Notice of Allowance dated Jul. 13, 2023 in Chinese Patent Application No. 201780034227X, and machine English translation thereof.
Corrected Notice of Allowability dated Jul. 27, 2023 in U.S. Appl. No. 17/361,774.
Office Action mailed Aug. 3, 2023 in U.S. Appl. No. 17/883,905.
Office Action dated Feb. 7, 2023 in Canadian Patent Application No. 3147251.
Office Action dated Aug. 17, 2023 in Japanese Patent Application No. 2022-140686, with English translation thereof.
Response to First Examination Report filed Sep. 7, 2023 in Indian Patent Application No. 202248072569.
Notice of Allowance dated Nov. 26, 2021 in Korean Patent Application No. 10-2021-7005394, with machine English translation thereof.
Office Action dated Dec. 9, 2021 in Japanese Patent Application No. 2021-002191, and English translation thereof.
Office Action dated Dec. 13, 2021 in Chinese Patent Application No. 2018113777986, and machine English translation thereof.
Partial European Search Report and Provisional Opinion dated Jan. 5, 2022 in European Patent Application No. 21 201 099.5.
Notice of Allowance dated Jan. 6, 2022 in Chinese Patent Application No. 2016800526048, and machine English translation thereof.
Zhigao, Hao, "Dual-channel disease in the atrioventricular node," International Journal of Cardiovascular Diseases, 1989, p. 248, vol. No. 1990083, and machine English translation thereof.
Iliescu, Radu, et al. "Mechanisms of Blood Pressure Reduction by Prolonged Activation of the Baroreflex," 31st Annual International Conference of the IEEE EMBS, Minneapolis, Minnesota, USA, Sep. 2-6, 2009, p. 2040-2042.
Response to Second Office Action filed Nov. 4, 2021 in Chinese Patent Application No. 2016800526048, and English translation thereof.
Amendment filed Dec. 3, 2021 in U.S. Appl. No. 16/431,776.
Response to Office Action filed Dec. 9, 2021 in U.S. Appl. No. 16/583,371.
Office Action mailed Dec. 21, 2021 in U.S. Appl. No. 16/663,573.
Response to Office Action filed Dec. 22, 2021 in Japanese Patent Application No. 2020-189356, with machine English translation thereof.
Response to Second Office Action filed Jan. 5, 2022 in Canadian Patent Application No. 2933278.
Response to First Examination Report filed Jan. 20, 2022 in Australian Patent Application No. 2017252310.
Notice of Allowance mailed Jan. 26, 2022 in U.S. Appl. No. 16/583,371.
Amendment filed Dec. 20, 2023 in U.S. Appl. No. 17/882,811.
Notice of Allowance mailed Dec. 20, 2023 in U.S. Appl. No. 17/883,905.
First Examination Report dated Dec. 21, 2023 in Australian Patent Application No. 2022246435.
Notice of Allowance mailed Jan. 10, 2024 in U.S. Appl. No. 17/882,811.
Response to Office Action filed Jan. 17, 2024 in Canadian Patent Application No. 3147251.
Office Action dated Feb. 15, 2024 in Japanese Patent Application No. JP2022-140686, with machine English translation thereof.
Intimation of Grant and Patent Certificate No. 514118 dated Feb. 22, 2024 in Indian Patent Application No. 201847012769.
Intimation of Grant and Patent Certificate No. 516531 dated Feb. 28, 2024 in Indian Patent Application No. 202248006588.
Corrected Notice of Allowability dated Mar. 13, 2024 in U.S. Appl. No. 17/882,811.
Corrected Notice of Allowability dated Mar. 27, 2024 in U.S. Appl. No. 17/883,905.
Office Action dated Apr. 8, 2024 in U.S. Appl. No. 18/545,095.
Second Office Action dated Apr. 5, 2024 in Canadian Patent Application No. 3021336.

Office Action dated Apr. 23, 2024 in U.S. Appl. No. 18/334,436.
Corrected Notice of Allowability dated Apr. 24, 2024 in U.S. Appl. No. 17/882,811.
Response to Extended European Search Report and Written Opinion dated May 7, 2024 in European Patent Application No. 23181110.0.
Office Action dated May 22, 2024 in U.S. Appl. No. 18/446,671.
Response to First Examination Report dated May 31, 2024 in Australian Patent Application 2022246435.
Second Examination Report dated Jun. 20, 2024 in Australian Patent Application No. 2022246435.
Request for Reconsideration dated Jun. 28, 2024 in U.S. Appl. No. 18/545,095.
U.S. Appl. No. 18/610,418, filed Mar. 20, 2024.
U.S. Appl. No. 18/636,466, filed Apr. 16, 2024.
Office Action dated Jul. 22, 2024 in U.S. Appl. No. 18/545,095.
Amendment filed Jul. 23, 2024 in U.S. Appl. No. 18/334,436.
Response to Office Action dated Jul. 29, 2024 in Canadian Patent Application No. 3021336.
EPO Communication dated Jul. 31, 2024 in European Patent Application No. 23181110.0.
Office Action dated Aug. 5, 2024 in U.S. Appl. No. 18/545,095.
Office Action dated May 9, 2024 in Canadian Patent Application No. 3184556.
Response to Office Action dated Aug. 9, 2024 in Japanese Patent Application No. 2022-169807, and machine English translation thereof.
Amendment filed Aug. 22, 2024 in U.S. Appl. No. 18/446,671.
Response to EPO Communication filed Aug. 28, 2024 in European Patent Application No. 23181110.0.
Office Action dated Aug. 6, 2024 in Canadian Patent Application No. 3147251.
Response to Office Action dated Sep. 6, 2024 in Canadian Patent Application No. 3184556.
Notice of Allowance mailed Sep. 18, 2024 in U.S. Appl. No. 18/334,436.
Corrected Notice of Allowability dated Oct. 9, 2024 in U.S. Appl. No. 18/334,436.
Response to Second Examination Report filed Oct. 11, 2024 in Australian Application No. 2022246435.
Notice of Allowance mailed Oct. 30, 2024 in U.S. Appl. No. 18/446,671.
Interview Summary mailed Oct. 31, 2024 in U.S. Appl. No. 18/545,095.
Amendment filed Nov. 4, 2024 in U.S. Appl. No. 18/545,095.
Third Examination Report dated Nov. 11, 2024 in Australian Patent Application No. 2022246435.
Final Office Action dated Nov. 14, 2024 in Japanese Patent Application No. 2022-140686 and machine English translation thereof.
Corrected Notice of Allowability dated Nov. 14, 2024 in U.S. Appl. No. 18/334,436.
Corrected Notice of Allowability dated Nov. 21, 2024 in U.S. Appl. No. 18/446,671.
Notice of Allowance mailed Dec. 4, 2024 in U.S. Appl. No. 18/545,095.
Response to Office Action filed Dec. 6, 2024 in Canadian Patent Application No. 3147251.
Response to Third Examination Report filed Dec. 6, 2024 in Australian Application No. 2022246435.
Notification Concerning Transmittal of International Preliminary Report on Patentability (IPRP) dated Dec. 5, 2024 in International Application No. PCT/US2023/067392.
Notification Concerning Transmittal of International Preliminary Report on Patentability (IPRP) dated Dec. 12, 2024 in International Application No. PCT/US2023/067649.
Notice of Acceptance dated Dec. 16, 2024 in Australian Patent Application No. 2022246435.
Corrected Notice of Allowability dated Dec. 27, 2024 in U.S. Appl. No. 18/334,436.
Corrected Notice of Allowability dated Feb. 3, 2025 in U.S. Appl. No. 18/446,671.
Intimation of Grant and Patent Certificate No. 559929 dated Feb. 11, 2025 in Indian Patent Application No. 202148037573.
Office Action dated Feb. 11, 2025 in U.S. Appl. No. 18/636,466.
Corrected Notice of Allowability dated Feb. 12, 2025 in U.S. Appl. No. 18/545,095.

(56)                    References Cited

OTHER PUBLICATIONS

Office Action dated Feb. 21, 2025 in U.S. Appl. No. 18/151,574.
Decision to Grant a Patent dated Feb. 27, 2025 in Japanese Patent
No. 2023-201290, and English translation thereof.
Decision to Grant a Patent dated Aug. 14, 2025 in Japanese Patent
Application No. 2022-140686, with English Translation thereof.
Notice of Allowance dated Aug. 19, 2025 in Canadian Patent
Application No. CA3147251.
Notice of Allowance dated Aug. 19, 2025 in Canadian Patent
Application No. CA3021336.
Notice of Allowance dated Aug. 21, 2025 in Canadian Patent
Application No. CA3184556.
Response to EPO Communication filed Sep. 2, 2025 in European
Patent Application No. 23181110.0.
Corrected Notice of Allowability dated Aug. 18, 2025 in U.S. Appl.
No. 18/151,574.
Corrected Notice of Allowability dated Sep. 18, 2025 in U.S. Appl.
No. 18/151,574.
Corrected Notice of Allowability dated Aug. 27, 2025 in U.S. Appl.
No. 18/636,466.
Corrected Notice of Allowability dated Oct. 9, 2025 in U.S. Appl.
No. 18/636,466.
Office Action mailed on Oct. 7, 2025 in European Patent Applica-
tion No. 23181110.0.
Certificate of Grant dated Apr. 17, 2025 in Australian Patent
Application No. 2022246435.
Amendment filed May 7, 2025 in U.S. Appl. No. 18/636,466.
Response to Office Action filed May 13, 2025 in Japanese Patent
Application No. 2022-140686, with English Translation of Amended
Claims and English Machine Translation of Remarks.
Amendment filed May 16, 2025 in U.S. Appl. No. 18/151,574.
Interview Summary mailed May 21, 2025 in U.S. Appl. No.
18/151,574.
Intimation of Grant and Patent Certificate No. 566889 dated May
29, 2025 in Indian Patent Application No. 202248072569.
Notice of Allowance mailed Jun. 11, 2025 in U.S. Appl. No.
18/151,574.
Notice of Allowance mailed Jul. 1, 2025 in U.S. Appl. No. 18/636,466.
EPO Communication dated Aug. 4, 2025 in European Patent
Application No. 23181110.0.

* cited by examiner

Atrial Pacing

401

402

403

Ventricular Pacing

405

METHODS AND APPARATUS TO STIMULATE HEART ATRIA

This application is a continuation of U.S. application Ser. No. 16/794,478, filed Feb. 19, 2020, now U.S. Pat. No. 11,529,520, issued Dec. 20, 2022, which is a division of U.S. application Ser. No. 15/226,056, filed Aug. 2, 2016, now U.S. Pat. No. 10,596,380, issued Mar. 24, 2020, which is a continuation of U.S. application Ser. No. 13/957,499, filed Aug. 2, 2013, now U.S. Pat. No. 9,427,586, issued Aug. 30, 2016, which is a continuation of U.S. application Ser. No. 12/987,498, filed Jan. 10, 2011, now U.S. Pat. No. 8,515,536, issued Aug. 20, 2013, which is a continuation of U.S. application Ser. No. 11/861,019, filed Sep. 25, 2007, now U.S. Pat. No. 7,869,874, issued Jan. 11, 2011, which claims the benefit of U.S. Provisional Application No. 60/826,847, filed Sep. 25, 2006, all of which are herein incorporated by reference in their entirety.

BACKGROUND

The present invention generally relates to implantable devices for cardiac stimulation and pacing therapy, and more particularly, the present invention is concerned with cardiac therapies involving the controlled delivery of electrical stimulations to the heart for the treatment of hypertension, congestive heart failure, and an apparatus for delivering such therapies with the objective of altering sympathetic and parasympathetic nerve stimulation and secretion of hormones by the heart muscle and to cause vasodilatation of blood vessels.

CONGESTIVE HEART FAILURE

Congestive heart failure (CHF) occurs when muscle cells in the heart die or no longer function properly, causing the heart to lose its ability to pump enough blood through the body. Heart failure usually develops gradually, over many years, as the heart becomes less and less efficient. It can be mild, scarcely affecting an individual's life, or severe, making even simple activities difficult.

Congestive heart failure (CHF) accounts for over 1 million hospital admissions yearly in the United States (U.S.) and is associated with a 5-year mortality rate of 40%-50%. In the U.S., CHF is currently the most costly cardiovascular disease, with the total estimated direct and indirect costs approaching $56 billion in 1999.

Recent advances in the treatment of CHF with medications, including angiotensin-converting enzyme (ACE) inhibitors, beta-blockers (Carvedilol, Bisoprolol, Metoprolol), Hydralazine with nitrates, and Spironolactone have resulted in significantly improved survival rates. Although many medications have been clinically beneficial, they fall short of clinician's expectations and as a result consideration has turned to procedures and devices as additional and more potent heart failure therapy.

There has been recent enthusiasm for biventricular pacing (pacing both pumping chambers of the heart) in congestive heart failure patients. It is estimated that 30% to 50% of patients with CHF have inter-ventricular conduction defects. These conduction abnormalities lead to a discoordinated contraction of the left and right ventricles of an already failing and inefficient heart. When the right ventricle alone is paced with a pacemaker, the delayed activation of the left ventricle, can also lead to significant dyssynchrony (delay) in left ventricular contraction and relaxation.

Because ventricular arrhythmias continue to threaten CHF patients and many anti-arrhythmic drugs have unacceptable side effects, a sophisticated implantable cardioverter-defibrillator (ICD) device has shown encouraging results. Biventricular pacing in combination with ICDs demonstrates a trend toward improved survival. Preliminary data in animals and humans using subthreshold (of the type that does not by itself cause heart muscle to contract) stimulation of the heart muscle to modulate cardiac contractility are encouraging and may further enhance the quality of life of CHF patients.

It is also clear that many patients with CHF are not candidates for biventricular pacing or do not respond to this treatment strategy. This also applies to other recent advances and experimental therapies. There is a clear need for new, better therapies that will improve and prolong life of heart failure patients and reduce the burden on the medical system. It is particularly important that these new therapies should not require a major surgery, prolonged stay in the hospital or frequent visits to the doctor's office.

HYPERTENSION

It is generally accepted that high blood pressure (HBP, also called hypertension) is bad, but most people don't know why, and what the term really means. In fact, all humans have high blood pressure some of the time, and we wouldn't be able to function if we didn't (such as during exercise). High blood pressure is only of concern when it persists for long periods of time or is extremely high over a very short (hours) period of time. Its adverse effects usually take many years to develop. Clinically important HBP is very common. According to official government figures, it affects 50 million people in the United States.

While everyone has high blood pressure some of the time, many people live their entire lives with moderately high blood pressure and never know it until it is notice on a routine visit to the doctor. Unfortunately, not all people are so lucky. In these people, high blood pressure significantly increases the risk of a number of serious events, mainly strokes and heart attacks.

More specifically, the damage caused by high blood pressure is of three general sorts. The first is the one everyone thinks of—bursting a blood vessel. While this is dramatic and disastrous when it happens, it's actually the least common of the three problems. It occurs most frequently in the blood vessels of the brain, where the smaller arteries may develop a weak spot, called an aneurysm. This is an area where the wall is thinner than normal and a bulge develops. When there is a sudden surge of pressure the aneurysm may burst, resulting in bleeding into the tissues. If this occurs in the brain, it is called a stroke. In contrast, if this happens to the aorta (the main blood vessel in the body), it is called a ruptured aortic aneurysm. Both of these events can lead to permanent damage and death.

The second adverse consequence of high blood pressure is that it accelerates the deposition of cholesterol in the arteries forming a blockage. This problem, too, takes many years to develop, and it is very difficult to detect until it causes a major blockage. The most important sites to be affected are the heart, where the blockage can cause angina and heart attacks; the brain, where it causes strokes; the kidneys, where it causes renal failure (and can also make the blood pressure go even higher); and the legs, where it causes a condition known as intermittent claudication, which means pain during walking and may even lead to losing a limb.

Third, high blood pressure puts a strain on the heart: Because it has to work harder than normal to pump blood against a higher pressure, the heart muscle enlarges, just as any other muscle does when it is used excessively. Over a long period of time, the high blood pressure can lead to congestive heart failure, the most frequent cause for hospitalization in the United States. Whatever the underlying cause, when the blood pressure reaches a certain level for a sufficient length of time it sets off a vicious cycle of damage to the heart, brain, and kidneys, resulting in further elevation of the pressure.

Classification of hypertension by its severity is somewhat arbitrary because there's no precise level of pressure above which it suddenly becomes dangerous. Historically, blood pressure has been primarily classified according to the height of the diastolic pressure. Someone whose diastolic pressure runs between 90 and 95 mm Hg may be regarded as having borderline hypertension, and when it's between 95 and 110 mm Hg, it's considered moderate, and at any higher levels, it's termed severe. Recent data suggests that the systolic pressure is as, and maybe more important than, diastolic blood pressure in determining the patient's risk for serious adverse events. Systolic hypertension is mainly seen in people over the age of 65 and is characterized by a high systolic, but normal diastolic, pressure (a reading of 170/80 mm Hg would be typical). It's caused by an age-related loss of elasticity of the major arteries. Another form of HBP, Labile hypertension, is a commonly used term for describing people whose pressure is unusually labile or variable. The most dangerous type of HBP is called malignant hypertension or high blood pressure with evidence on physical exam that this pressure causing an acute deleterious affecting on vital organ function. Malignant hypertension is regarded as an emergency requiring immediate treatment in a hospital. Not surprisingly, if untreated, malignant hypertension can be rapidly fatal. Although more people are treated with drugs nowadays than before, malignant hypertension is still common.

The objective of treatment is not simply to lower the blood pressure, but to prevent its consequences, such as strokes and heart attacks. According to the American Heart Association high blood pressure is present in 50,000,000 Americans (Defined as systolic pressure 140 mm Hg or greater, and/or diastolic pressure 90 mm Hg or greater, or taking antihypertensive medication). Of those with HBP, 31.6 percent are unaware they have it; 27.4 percent are on medication and have it controlled; 26.2 percent are on medication but don't have their HBP under control; and 14.8 percent aren't on medication. In most cases, high blood pressure can be controlled with one or a combination of oral drugs. Of those patients that take medication to control HBP, many suffer from debilitating side effects of these drugs such as heart arrhythmias, inability to exercise or do normal activities of daily living and impotence.

ELECTRIC ACTIVITY OF THE HEART

In a given cardiac cycle (corresponding to one "beat" of the heart), the two atria contract, forcing the blood therein into the ventricles. A short time later, the two ventricles contract, forcing the blood therein to the lungs (from the right ventricle) or through the body (from the left ventricle). Meanwhile, blood from the body refills the right atrium and blood from the lungs refills the left atrium, waiting for the next cycle to begin. A healthy adult human heart may beat at a rate of 60-80 beats per minute (bpm) while at rest, and may increase its rate to 140-180 bpm when the adult is engaging in strenuous physical exercise, or undergoing other physiologic stress.

The healthy heart controls its rhythm from its sinoatrial (SA) node, located in the upper portion of the right atrium. The SA node generates an electrical impulse at a rate commonly referred to as the "sinus" or "intrinsic" rate. This impulse is delivered from the SA node to the atrial tissue when the atria are intended to contract. The electrical signal continues to propagate from the atrial tissue through the atrioventricular (AV) node, a specialized collection of tissue that serves as a "gatekeeper" for the impulses traveling between the atria and the ventricles. After a suitable delay (on the order of 140-220 milliseconds), the signal finally propagates to the ventricular tissue and the ventricles are stimulated to contract. SA node is the natural pacemaker of the heart. If it is disabled, there are other specialized areas of the heart muscle that can generate an intrinsic heart rate.

The ventricular muscle tissue is much more massive than the atrial muscle tissue. The atrial muscle tissue need only produce a contraction sufficient to move the blood a very short distance from the respective atrium to its corresponding ventricle. The ventricular muscle tissue, on the other hand, must produce a contraction sufficient to push the blood through the complete circulatory system of the entire body. Even though total loss of atrial contraction can lead to a small reduction of cardiac output it is not an immediate risk to life. Conversely, the atria of the heart can sustain a higher number of contractions per minute than the ventricles without endangering life.

ELECTRONIC CARDIAC PACEMAKERS

It is the function of a electronic pacemaker (pacemaker) to provide electrical stimulation pulses to the appropriate chamber(s) of the heart (atrium, ventricle, or both) in the event the heart is unable to beat on its own (i.e., in the event either the SA node fails to generate its own natural stimulation pulses at an appropriate sinus rate, or in the event such natural stimulation pulses do not effectively propagate to the appropriate cardiac tissue). Most modern pacemakers accomplish this function by operating in a "demand" mode where stimulation pulses from the pacemaker are provided to the heart only when it is not beating on its own, as sensed by monitoring the appropriate chamber of the heart for the occurrence of a P-wave or an R-wave. If a P-wave or an R-wave is not sensed by the pacemaker within a prescribed period of time (which period of time is often referred to as the "escape interval"), then a stimulation pulse is generated at the conclusion of this prescribed period of time and delivered to the appropriate heart chamber via a pacemaker lead. Pacemaker leads are isolated wires equipped with sensing and stimulating electrodes.

Modern programmable pacemakers are generally of two types: (1) single-chamber pacemakers, and (2) dual-chamber pacemakers. In a single-chamber pacemaker, the pacemaker provides stimulation pulses to, and senses cardiac activity within, a single-chamber of the heart (e.g., either the right ventricle or the right atrium). In a dual-chamber pacemaker, the pacemaker provides stimulation pulses to, and senses cardiac activity within, two chambers of the heart (e.g., both the right atrium and the right ventricle). The left atrium and left ventricle can also be paced, provided that suitable electrical contacts are made therewith.

Much has been written and described about the various types of pacemakers and the advantages and disadvantages of each. For example, U.S. Pat. No. 4,712,555 of Thornander et al. and U.S. Pat. No. 5,601,613 of Florio et al. present background information about pacemakers and the manner in which they interface with a patient's heart. These patents are hereby incorporated by reference in their entirety.

One of the most versatile programmable pacemakers available today is the DDDR pacemaker. This pacemaker represents a fully automatic pacemaker which is capable of sensing and pacing in both the atrium and the ventricle, and is also capable of adjusting the pacing rate based on one or more physiological factors, such as the patient's activity level. It is commonly accepted that the DDDR pacemaker is superior in that it can maintain AV synchrony while providing bradycardia (slow heart beat) support. It is also generally more expensive than other, simpler types of pacemakers. A description of DDDR pacing is included in this disclosure as a state of the art.

In general, DDDR pacing has four functional states: (1) P-wave sensing, ventricular pacing (PV); (2) atrial pacing, ventricular pacing (AV); (3) P-wave sensing, R-wave sensing (PR); and (4) atrial pacing, R-wave sensing (AR).

It is accepted as important and advantageous, for the patient with complete or partial heart block, that the PV state of the DDDR pacemaker tracks the atrial rate, which is set by the heart's SA node, and then paces in the ventricle at a rate that follows this atrial rate. It is assumed that because the rate set by the SA node represents the rate at which the heart should beat in order to meet the physiologic demands of the body (at least for a heart having a properly functioning SA node) the rate maintained in the ventricle by such a pacemaker is truly physiologic.

In some instances, a given patient may develop dangerously fast atrial rhythms, which result from a pathologic arrhythmia such as a pathological tachycardia, fibrillation or flutter. In these cases, a DDDR pacemaker may pace the ventricle in response to the sensed atrial arrhythmia up to a programmed maximum tracking rate (MTR). The MTR defines the upper limit for the ventricular rate when the pacemaker is tracking the intrinsic atrial rate. As a result, the MTR sets the limit above which the ventricles cannot be paced, regardless of the intrinsic atrial rate. Thus, the purpose of the MTR is to prevent rapid ventricular stimulation, which could occur if the intrinsic atrial rate becomes very high and the pacemaker attempts to track atrial activity with 1:1 AV synchrony.

When the intrinsic atrial rate exceeds the MTR the pacemaker may initiate one or more upper atrial rate response functions—such as automatically switching the pacemaker's mode of operation from an atrial tracking mode to a non-atrial rate tracking mode.

The heart's natural response to a very high atrial rate involves a natural phenomenon known as "blocking"— where the AV node attempts to maintain a form of AV synchrony by "dropping out" occasional ventricular beats when the high atrial rate exceeds a certain natural threshold i.e., the refractory period of the heart tissue. The blocking phenomenon is often expressed as a ratio of the atrial beats to the ventricular beats (e.g. 6:5, 4:3, etc.). Of particular importance is a 2:1 block condition where there are two atrial beats for every one ventricular beat. The 2:1 block condition is a natural response to a very high atrial rate, during which full ventricular rate synchronization (i.e. at a 1:1 ratio) would be dangerous to the patient.

Some known pacemakers emulate this 2:1 condition, by tracking P-waves up to the device's programmed total refractory period (TARP) of the heart. That is, P-waves which fall in the total refractory period are not tracked, and the device is said to have a "2:1 response mode". During the 2:1 block response mode, the ventricles are paced at a lower rate than the natural atrial rate, because P-waves occurring soon after ventricular events are ignored for the purposes of calculating the ventricular pacing rate. As a result, the 2:1 block response mode prevents the pacemaker from pacing the ventricles at a tachycardia rate.

The 2:1 block response mode is an effective response for dealing with short incidences of high atrial rates and in preventing occurrence of a pacemaker mediated tachycardia resulting from retrograde P-waves. However, the 2:1 block response mode may become uncomfortable for the patient if it is maintained for an extended period of time due to programmed long atrial refractory periods, because the pacing rate will be ½ of the required physiologic rate.

Many more advanced pacemaker operation modes have been described and sometimes implemented. Some of these modes included sensing abnormally high atrial rates and prevented them from causing rapid ventricular rates. Common to prior pacing no attempt has been made to induce a rapid (faster than normal) atrial rate by pacing or to pace atria at rate higher than ventricles.

PACEMAKER SYNDROME

Although pacemakers provide relief from life-threatening arrhythmias and can improve quality of life significantly, they also can function in a nonphysiologic manner, which is accompanied by nontrivial morbidity. Pacemakers functioning in the VVI mode (e.g., a pacing mode in which of the native atrial electrical or contractile state are not sensed and ignored by the pacemaker) have been noted to sacrifice the atrial contribution to ventricular output. In some instances, and because of this lack of feedback, the timing of native atrial contraction and pacemaker-induced ventricular contraction is such that the atrial contraction occurred during ventricular contraction or against closed atrioventricular (A-V) valves (Tricuspid and Mitral), producing reverse blood flow and nonphysiologic pressure waves. The A-V valves normally open passively whenever the pressure in the atrium exceeds the pressure in the ventricle. The pressure in the ventricles is low during ventricular diastole (or the normal termed ventricular filling period). In the case of non-physiological pacing, the A-V valves are not able to be normally opened by the pressure in the atrium during atrial contraction as the ventricles are in their pumping period (called ventricular systole) and the pressure in the ventricles significantly exceeds the maximum possible pressure able to be generated in the atria. This abnormal, non-physiological relationship of atrial to ventricular contraction can occur in other pacing modes if a patient's heart tissue is susceptible to allowing abnormal retrograde (e.g., from the ventricle to the atria) conduction of native or pacemaker-induced ventricular electrical activity.

Pacemaker syndrome was first described as a collection of symptoms associated with right ventricular pacing. Since its first discovery, there have been many definitions of pacemaker syndrome, and the understanding of the cause of pacemaker syndrome is still under investigation. In a general sense, pacemaker syndrome can be defined as the symptoms associated with right ventricular pacing relieved with the return of A-V and V-V synchrony. Recently, most authors have recognized that pacemaker syndrome, which initially was described in patients with ventricular pacemakers, is related to nonphysiologic timing of atrial and ventricular contractions, which may occur in a variety of pacing modes. Some have proposed renaming the syndrome "A-V dyssynchrony syndrome," which more specifically reflects the mechanism responsible for symptom production.

The symptoms of pacemaker syndrome included dyspnea (shortness of breath) and even syncope (fainting). Syncope is temporary loss of consciousness and posture, described as "fainting" or "passing out." It's usually related to temporary insufficient blood flow to the brain. It's a common problem, accounting for 3 percent of emergency room visits and 6 percent of hospital admissions. It most often occurs when 1) the blood pressure is too low (hypotension) and/or 2) the heart doesn't pump a normal supply of blood to the brain.

In pacemaker syndrome patients, syncope occurs secondary to retrograde, ventricular to atrial (V-A) conduction resulting in the contraction of the atria against closed A-V valves. One effect of the elevated atrial and venous pressures associated with the contraction against closed A-V valves is to cause a vagal afferent response resulting in peripheral vasodilatation leading to a marked lowering of blood pressure (termed hypotension). Syncope is usually associated with systolic blood pressure declines of greater than 20 mm Hg that can occur with the onset of pacing.

Pacemaker syndrome can also lead to decreased cardiac output, with resultant increase in left atrial pressure and left ventricular filling pressure. Not only can this decrease in blood flow lead to syncope, this increase in atrial pressure or ventricular filling pressure can also result in increased production of atrial natriuretic peptide (ANP) and B-type natriuretic peptide (BNP). ANP and BNP are potent arterial and venous vasodilators that can override carotid and aortic baroreceptor reflexes attempting to compensate for decreased blood pressure. Patients with pacemaker syndrome exhibit increased plasma levels of ANP, and patients with so called atrial pressure "cannon a waves" (cause by atrial contraction against a closed valve) have higher plasma levels of ANP than those without "cannon a waves".

NATRIURETIC PEPTIDES (ANP AND BNP)

Atrial natriuretic peptide (ANP) is a hormone that is released from myocardial cells in the atria and in some cases the ventricles in response to volume expansion and increased wall stress. Brain natriuretic peptide (BNP) is a natriuretic hormone that is similar to ANP. It was initially identified in the brain but is also present in the heart, particularly the ventricles.

The release of both ANP and BNP is increased in heart failure (CHF), as ventricular cells are recruited to secrete both ANP and BNP in response to the high ventricular filling pressures. The plasma concentrations of both hormones are increased in patients with asymptomatic and symptomatic left ventricular dysfunction, permitting their use in diagnosis. A Johnson and Johnson Company Scios sells popular intravenous (IV) medication Natrecor (nesiritide), a recombinant form of the endogenous human peptide for the treatment of decompensated CHF. The advent of Natrecor marked an important evolution in the understanding and treatment of acute heart failure.

Both ANP and BNP have diuretic, natriuretic, and hypotensive effects. They also inhibit the renin-angiotensin system, endothelin secretion, and systemic and renal sympathetic activity. Among patients with CHF, increased secretion of ANP and BNP may partially counteract the effects of norepinephrine, endothelin, and angiotensin II, limiting the degree of vasoconstriction and sodium retention. BNP may also protect against collagen accumulation and the pathologic remodeling that contributes to progressive CHF.

SUMMARY

It has been observed that—while clearly deleterious to the majority of heart disease patients—the phenomenon of the reduction of blood pressure in response to nonphysiologic pacing can be beneficial by reducing blood pressure in the group of patients with severe hypertension and particularly ones with malignant drug refractory hypertension that frequently results in strokes and sudden death.

The inventors have developed a pacemaker that is counterintuitively used dissynchronously to generate different atrial and ventricular contraction rates. Specifically, a higher rate of atrial contractions than ventricular contractions is generated. It is understood that this may result in suboptimal performance of the heart. However, the inventors propose that this disadvantage of lower blood pressure from the reflex vasodilation caused by nonphysiologic pacing can paradoxically benefit some heart failure patients if the increased ANP-BNP secretion from increased atrial pressures sufficiently increases the release of ANP and BNP hormones to a level that overcomes potential detriments from reduced atrial contribution to cardiac output.

One Embodiment, AV Blocked Electric Stimulation of the Heart:

One embodiment disclosed here uses a modified implanted electronic cardiac pacemaker to increase ANP and BNP secretion by pacing the right atrium of the patient at an appropriately high rate. In the first described embodiment, patients have either a natural atrioventricular block (AV block) or have an AV block induced by heart tissue ablation or some other appropriate procedure. For example in patients with a so-called third-degree AV block (complete AV block, no AV conduction), no atrial impulses reach the ventricles, and ventricular rhythm is maintained by a subsidiary natural pacemaker. Since subsidiary pacemakers must be below the level of block, their location is in part determined by the site of block. In third-degree AV nodal block, the ventricular rhythm is usually maintained by pacemakers in the AV junction with resultant narrow QRS complexes. In third-degree AV block localized to the bundle branches, ventricular rhythm is maintained by a pacemaker in the Purkinje fibers, with resultant wide QRS complexes. The junctional pacemaker rate is usually faster (40-80 beats/min) compared with the peripheral Purkinje network (20-40 beats/min). In such patients, a dual chamber pacemaker can be used to pace atria at a rate much higher than the ventricles without the risk of patient developing dangerous ventricular tachycardia (rapid heart beat) as the atrial impulses, either native or pacemaker-induced, are not conducted to the ventricle. An atrioventricular (AV) node ablation is a known medical procedure that destroys a part of the heart's normal electrical system. The combination of pacing and AV node ablation is sometimes used clinically in patients with chronic atrial fibrillation and rapid ventricular response that poorly respond to drug therapy.

This is accomplished by cauterizing the AV node, which is located between the upper heart chamber (atria) and the lower heart chambers (ventricles). Once the AV node is cauterized, none or few impulses from the atria will be able to reach the ventricles. Currently, an AV node ablation is performed when the patient's rhythm disturbance (arrhythmia) originates in the atria and its effects on atrial or ventricular function cannot be controlled adequately with other measures. A permanent pacemaker is installed afterwards, to keep the heart beating at a normal rate. In this case, at least one pacemaker lead is connected directly to a ventricle.

Another Embodiment, Refractory Period Electric Stimulation of the Heart:

Inventors realized that it is desired to implement non-physiologic pacing with the purpose of increasing atrial wall stress and cause vagal reflex and hormonal release without blocking natural AV conduction. Inventors discovered that such pacing modality is possible utilizing naturally occurring periods in the electric cyclic activity of the heart when the heart muscle conduction is blocked by so called refractory periods.

In the heart are specialized tissue collections that have a unique property, they rhythmically emit electrical impulses. The cause of these phenomena is the "leaky membrane" that allows the regular exchange of Sodium, Potassium, and Calcium ions and causes a change in the polarization of the cells. Sodium ions move into the cell and start the depolarization, Calcium ions extend that depolarization. When the Calcium ions stop entering the cell Potassium ions move in and the repolarization of the cell begins. To simplify this, the Sodium starts the cells stimulation, the Calcium extends that stimulation to allow the entire muscle to contract before Potassium comes along and tells it to relax for a moment and get ready for the next wave. The most important aspect of the repolarization-depolarization cycle of the individual heart muscle elements that is relevant to this invention is the "refractory" period where the cells reset for the next wave and temporarily cannot be electrically stimulated to contract.

These atrial, AV and ventricular refractory periods have two stages, the Absolute and Relative refractory periods. In the Absolute refractory phase, the conduction system and heart muscle are in a "drained" state and need a moment to "recharge" to be able to electrically and/or mechanically respond to another electrical stimulus. Thus, a pacemaker impulse applied to these structure during this time would not be electrically conducted or cause the heart muscle to contract. In the relative refractory period that follows the absolute refractory period, the electrical conducting tissues and/or heart muscle cells are not fully "recharged" but may conduct and/or contract if excited with a strong pacing signal.

Refractory period of the atrial in the naturally beating heart begins and ends before the end of the absolute refractory period of the ventricle. Therefore, it is possible to generate an electrical stimulus to pace the atria of the heart during the ventricular refractory period and generate the atrial contraction but this electrical stimulus will not propagate through the AV node to the ventricle and cause a ventricular contraction.

To maximize the effect of the atrial contraction in the terms of maximum atrial muscle wall stress and the subsequent neural activation and hormonal release, it is desired to cause a contraction of the atrium when the atrium is filled with blood and its walls are distended. It is also desired to cause atrial contraction against the closed AV valve, causing the phenomenon similar to the pacemaker syndrome. This maximum stress in the atrial wall caused by the atrial contraction can be expected to result in the maximum vasodilatation of peripheral blood vessels that will achieve the desired reduction of systemic arterial blood pressure.

The atria of the heart naturally contract during the approximately 100 ms following the P-wave of the surface ECG of the heart. The Q-wave of the surface ECG corresponds to the beginning of the absolute refractory period of the atria. The atria passively fill with blood during the ventricular systole, which occurs following the Q-wave of the surface ECG. Approximately half-way or 100-150 ms into the ventricular systole period, the atria are fully expanded and primed with blood and the window of opportunity for the maximum benefit from nonphysiologic atrial pacing begins. The ventricles contracts during the ventricular systole of the heart and are absolutely refractory to electric stimulation during this period. Importantly, the atrial refractory period ends before the 50% of the ventricular systole has elapsed. The atria are now electrically and mechanically "armed" and can be triggered to contract by a pacing impulse. This window of opportunity can be defined as occurring from the end of the atrial refractory period (approximately 30 to 50% into the ventricular systole following the Q wave) and the end of the ventricular refractory period that corresponds to the middle of the T-wave, which is also the time when the aortic valve opens. During this time window, it is possible to apply a pacing signal to the atrium of the heart, generate a nonphysiologic atrial contraction without provoking the undesired nonphysiologic ventricular contraction. The timing diagram on the FIG. 5 of this application illustrates the principal of nonphysiologic atrial contraction.

In summary, inventors discovered that the following novel algorithm allows pacemaker stimulated atrial contraction in an intact naturally beating heart:

A. The end of atrial refractory period is detected or predicted, based on physiologic monitoring of the heart, for example by detecting suitable event points of the patient's surface ECG or intracardiac electrogram. The end of atrial refractory period also corresponds to the end of the depolarization and mechanical contractile activity of the atrial heart muscle.

B. The atrium is paced to contract following the end of the refractory period of the atrium but before the end of the refractory period of the ventricle, for example in the middle of ventricular systole.

C. In one proposed embodiment the resulting contraction of the atrium occurs in the later part of the ventricular systole when atrium is distended by passive filling with blood. A non-physiological, paced atrium contraction is then caused during this period which causes the atrium to contract against the closed AV valve, increasing atrial pressure and wall stress leading to beneficial neural and hormonal stimuli. These stimuli are expected to result in 1) peripheral vasodilatation and reduction of blood pressure in hypertensive patients or 2) increased ANP/BNP secretion leading to beneficial physiological and clinical sequelae in patients with CHF.

In one embodiment of the invention, a sensing and pacing lead of a pacemaker (implantable or temporary) is placed in an atrium (such as RA) of the heart. The intracardiac ECG is sensed for signs of atrial and ventricular depolarization and repolarization. The beginning and end of the atrial refractory period is predicted following a known delay after the P wave or R wave of the heart. For example, the atrium can be paced 150 milliseconds (ms) after the detected R wave. The desired delay can be recalculated by the embedded software based on the heart rate or set by the physician during the office visit of the patient. All modern pacemakers include suitable sensing, programmability and telemetry functions.

It is understood that there are many ways to detect various phases of the electric heart activity cycle using surface or intracardiac ECG, pressures, wall motion or heart sound sensors. It is imagined that some of these signals can be used to synchronize the proposed nonphysiologic pacing to the desired window of the heart cycle. Common to all of these potential embodiments, the heart atrium (right or left or both) is paced after the end of the atrial refractory period and before the end of the ventricular refractory period.

In this invention, a pacemaker is counter intuitively used dissynchronously to generate different atrial and ventricular contraction rates. Specifically, a higher rate of atrial contractions than ventricular contractions is generated. It is understood that this may result in suboptimal performance of the heart. The inventors propose that this disadvantage will be offset by the benefit of the increased beneficial vasodilatory stimulus and hormonal secretion by the heart atria in hypertensive and heart failure patients.

Electronic pacemakers are currently used to replace or supplement the natural pacing nodes of the heart by applying electric excitory signals to the heart muscle to cause contraction and blood pumping cycle. Pacemakers are used in patients with diseased nodes (slow heart beat) and defective (blocked) conduction pathways. Bi-ventricular pacemakers pace both ventricles of the heart to restore synchrony between the ventricles.

Generally, the conventional wisdom of all pacing therapies for the heart disease is as follows. A human heart consists of four chambers—two atria and two ventricles. In order for the heart to efficiently perform its function as a pump, the atrial muscles and ventricular muscles should contract in a proper sequence and in a timed relationship, as they do in a healthy heart. Therefore electronic pacemakers are used to restore the normal heartbeat or to restore synchrony between different chambers of the heart. It is understood that the methods and embodiments described in this patent may be incorporated into existing pacemaker devices, such as the pacemakers, biventricular pacemakers or ICDs.

A method for treating hypertension by pacing a heart of a patient having an atria and a ventricle has been developed, the method comprising: pacing at least one atrium of the heart, where the said atrial pacing occurs after the end of atrial refractory period, during the ventricular refractory period of the heart and results in an atrial contraction that is not immediately followed by a ventricular contraction. The method may include paced atrial contraction occurs against a closed AV valve of the heart. The method may further include sensing the ECG and detection of a P wave or an R wave followed a preset delay and the excitory pacing pulse. In addition, the method may include pacing that occurs between the R wave and before a middle of a T wave. In addition, the method may include pacing that occurs approximately 100 to 200 ms after the R wave. Further, the method may include pacing results in two atrial contractions per each ventricular contraction of the heart, where every second atrial contraction is nonphysiologic and paced. The method may include atrial pacing that occurs on every second heartbeat, or pacing that occurs approximately 250 to 350 ms after the P wave. The method may further include paced atrial contraction occurs against a closed AV valve of the heart in a middle of systole after substantial filling of the atria with blood.

SUMMARY OF THE DRAWINGS

A preferred embodiment and best mode of the invention is illustrated in the attached drawings that are described as follows.

DETAILED DESCRIPTION

Figure 1:
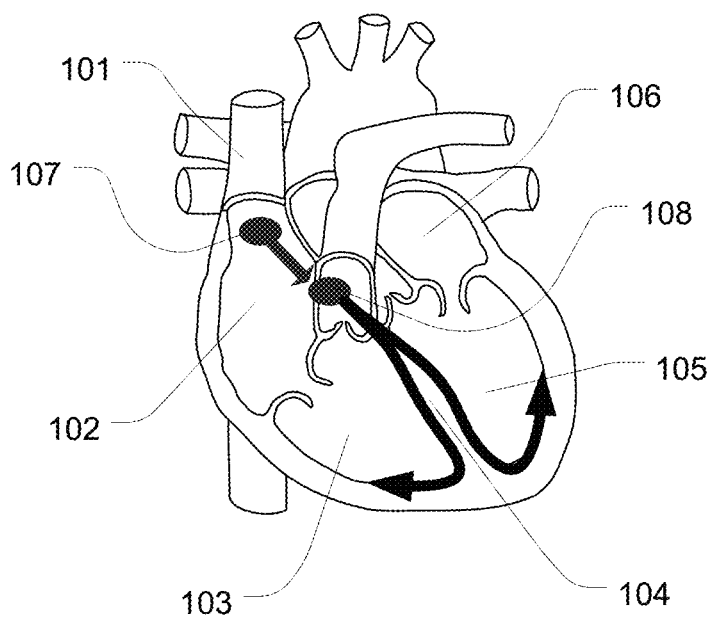
FIG. 1 illustrates the electric excitory pathways and chambers of a human heart.

FIG. 1 shows a normal heart. Electrical pulses in the heart are controlled by special groups of cells called nodes. The rhythm of the heart is normally determined by a pacemaker site called the sinoatrial (SA) node 107 located in the posterior wall of the right atrium 102 near the superior vena cava (SVC) 101. The SA node consists of specialized cells that undergo spontaneous generation of action potentials at a rate of 100-110 action potentials ("beats") per minute. This intrinsic rhythm is strongly influenced by autonomic nerves, with the vagus nerve being dominant over sympathetic influences at rest. This "vagal tone" brings the resting heart rate down to 60-80 beats/minute in a healthy person. Sinus rates below this range are termed sinus bradycardia and sinus rates above this range are termed sinus tachycardia.

The sinus rhythm normally controls both atrial and ventricular rhythm. Action potentials generated by the SA 107 node spread throughout the atria, depolarizing this tissue and causing right atrial 102 and left atrial 106 contraction. The impulse then travels into the ventricles via the atrioventricular node (AV node) 108. Specialized conduction pathways that follow the ventricular septum 104 within the ventricles rapidly conduct the wave of depolarization throughout the right 103 and left 105 ventricles to elicit the ventricular contraction. Therefore, normal cardiac rhythm is controlled by the pacemaker activity of the SA node and the delay in the AV node. Abnormal cardiac rhythms may occur when the SA node fails to function normally, when other pacemaker sites (e.g., ectopic pacemakers) trigger depolarization, or when normal conduction pathways are not followed.

Figure 2:
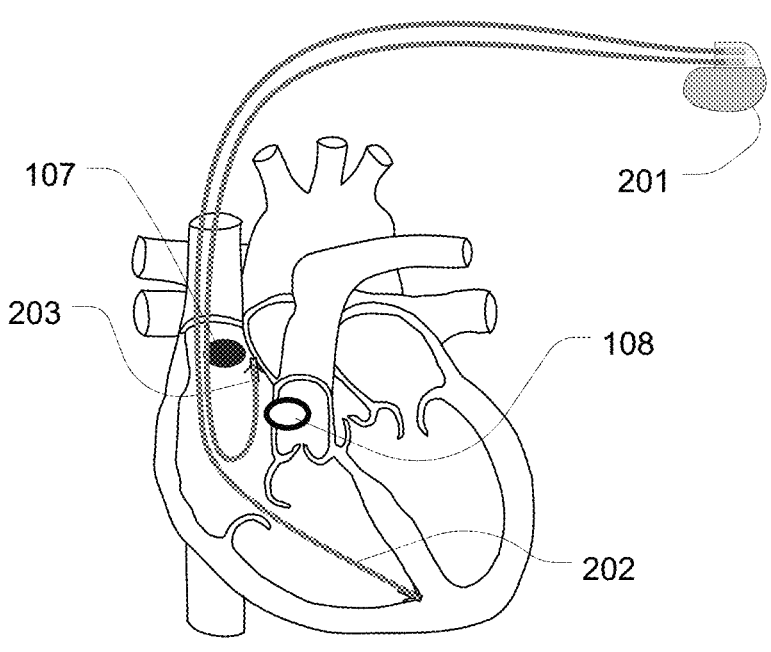
FIG. 2 illustrates the embodiment of the invention with a two lead pacing system.

FIG. 2 shows a heart treated with one embodiment of the invention. Pulse generator (pacemaker) 201 is implanted in a tissue pocket in the patient's chest under the skin. In this embodiment the generator 201 is connected to the heart muscle by two electrode leads. The ventricular lead 202 is in contact with the excitable heart tissue of the right ventricle 103. The atrial lead 203 is in contact with the excitable heart tissue of the right atrium 102. It is understood that the pacemaker can have more leads such as a third lead to pace the left ventricle 105. It is expected that in future cardiac pacemakers will have even more leads connecting them to various parts of the anatomy.

Leads 203 and 202 can combine sensing and pacing electrodes as known and common in the field. The atrial lead 203 can therefore sense the natural intrinsic contractions of the atria before they occur and communicate them to the generator 201. The generator is equipped with the programmable logic that enables it to sense signals, process the information, execute algorithms and send out electric signals to the leads.

In this embodiment the natural conduction path between the SA node 107 and the AV node 108 is blocked. The patient may already have a natural complete AV block. In this case no intervention is needed. If the patient has functional electric pathways from atria to ventricles, the patient's AV node can be disabled (blocked) by tissue ablation. It is understood that many irreversible and reversible methods of selectively blocking conduction in the heart are known. These include treatment with chemical agents and blocking with subthreshold electric stimulation (non-excitatory stimulation that does not cause muscle fibers to contract). Ablation of the AV node is used as an example since it is widely accepted and easily performed using RF energy catheters. Other devices that use cold, laser and ultrasound energy to perform ablation are also known.

Figure 3:
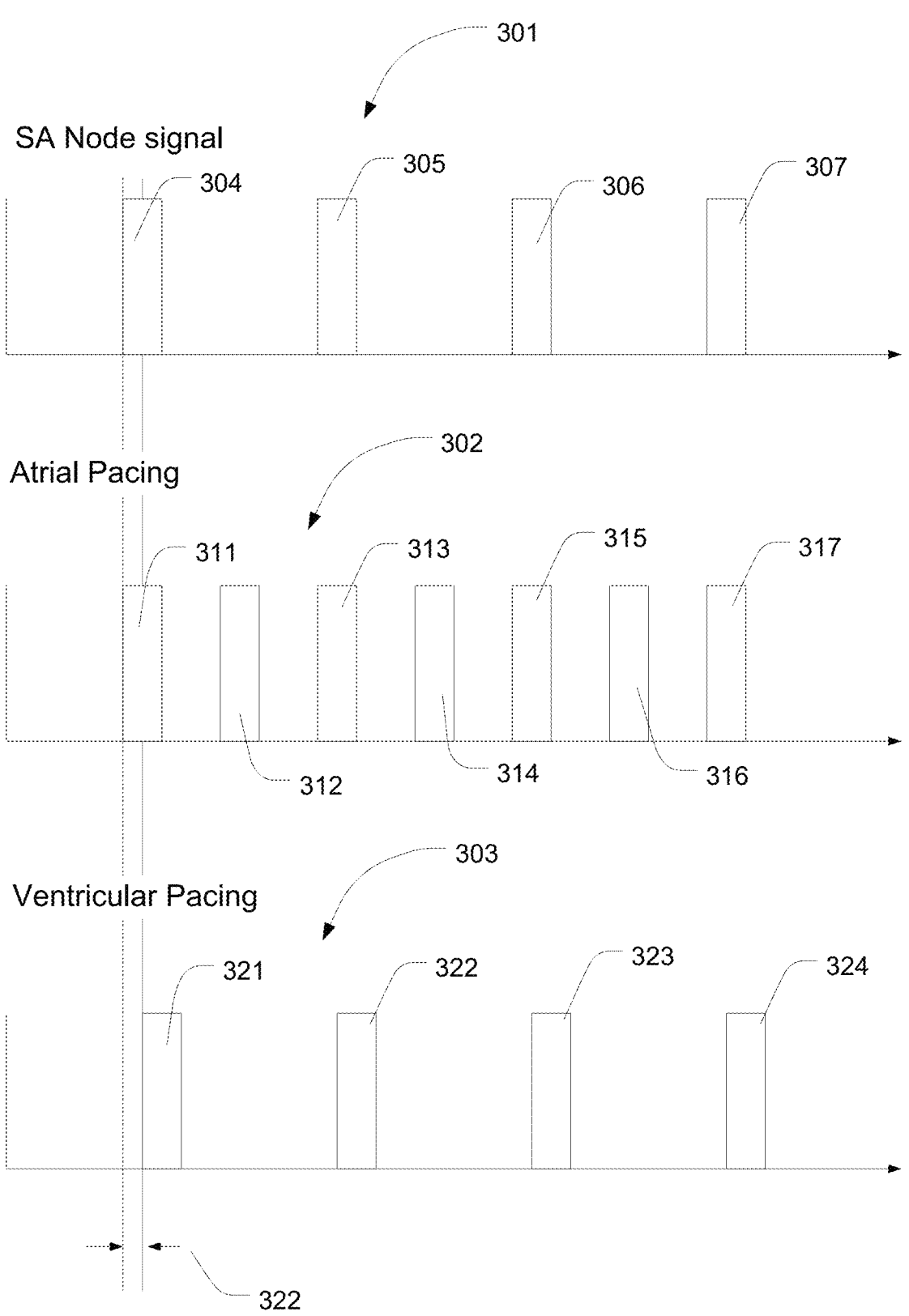
FIG. 3 illustrates one sequence of natural and induced stimulation pulses.

FIG. 3 illustrates one possible embodiment of the invention with a sequence of stimulation pulses. Pulses are simplified and presented as rectangular blocks spaced in time as represented by the X-axis.

Trace 301 illustrates the natural or intrinsic rate generated by the SA node of the heart. The SA node generates pulses 304, 305, 306 and 307. These pulses can be sensed by the atrial lead 203.

In response to the sensing of intrinsic atrial pulses, the pulse generator 201 generates a series of pulses represented by the trace 302. Pulses are conducted to the atria by the atrial lead 203. Device generated atrial stimulation pulses 311, 313, 315 and 317 are in synchrony with the SA node pulses 304, 305, 306 and 307. They represent the intrinsic heart rate. The generator 201 (based on an embedded algorithm) also generates extra atrial pulses 312, 314 and 316. Together synchronous pulses 311, 313, 315, 317 and asynchronous pulses 312, 314, 316 determine the atrial rate of the heart.

Trace 303 represents ventricular stimulation pulses 321, 322, 323 and 324 conducted to the ventricle of the heart by the ventricular lead 202. The AV node of the heart in this embodiment is blocked. Therefore the ventricular stimulation is generated by the generator 201 based on an embedded algorithm. To ensure better performance of the heart ventricular pulses 321, 322, 323 and 324 are synchronized to the synchronous atrial pulses 311, 313, 315 and 317 with a short delay 308 determined by the embedded algorithm that simulates the natural delay of the AV node conduction.

The algorithm illustrated by the FIG. 3 can be described as a following sequence:

a. sensing an intrinsic SA node pulse (P-wave), b. generating a synchronous atrial pacing pulse, c. calculating the intrinsic atrial rate based on previous SA node pulse intervals, d. generating synchronous ventricular pacing signal delayed from the synchronous atrial pacing signal at the ventricular rate equal to the intrinsic SA node excitation rate (sinus rhythm), e. calculating the desired increased atrial rate, such as for example, a 2:1 (A:V) rate, f. generating asynchronous atrial pacing signal based on the calculated increased atrial rate, and g. waiting for the next intrinsic SA node pulse (P-wave).

It is understood that this example of an algorithm is an illustration and many other embodiments of the invention can be proposed. It can be envisioned that more than 2:1 (atrial:ventricular) rate can be tolerated by the patient or that less than 2:1 rate is desired such as accelerating every second atrial beat.

It may be not essential to preserve the natural sinus rhythm (from the SA node). In some patients it may be desired for the algorithm to take over the heart rate and force all the atrial contraction. Pacing modalities that do not rely on the SA node to generate the heart rate are known and used to treat bradycardia. The SA node of a patient can be ablated similar to the AV node and the embedded pacemaker algorithm will pace the atria. Alternatively, atria may be paced if the natural SA node pulse is not senses within the expected time from the last ventricular contraction. Various activity sensors such as accelerometers can be used to accelerate the heart rate as needed.

Figure 4:
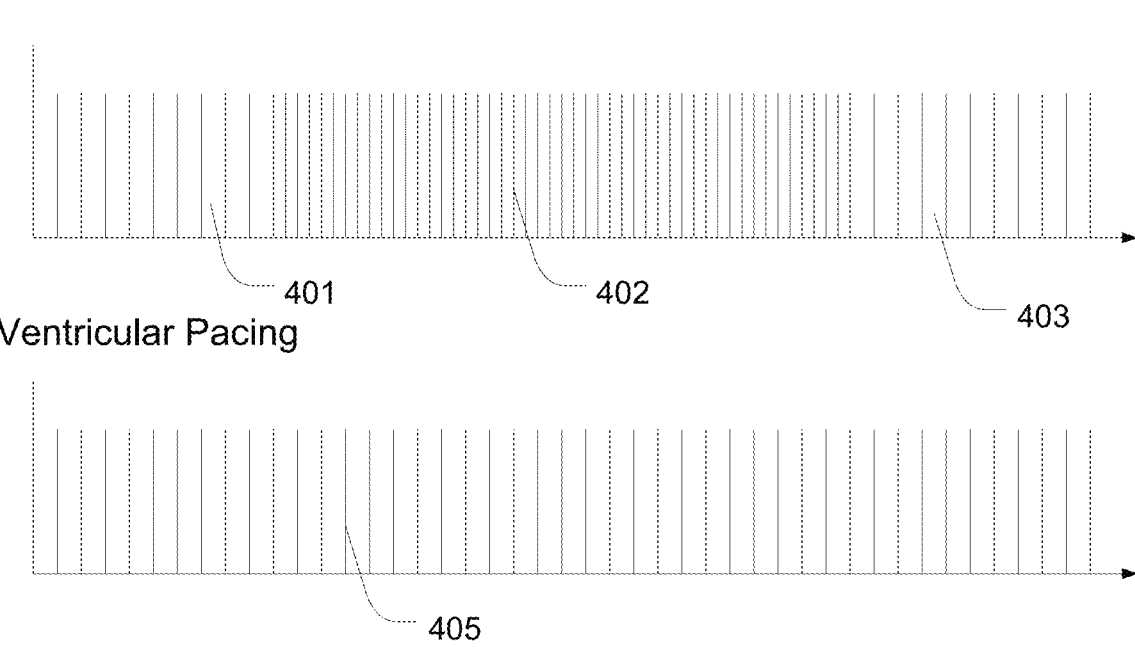
FIG. 4 illustrates intermittent asynchronous pacing.

FIG. 4 illustrates intermittent application of the proposed therapy. It is possible that some patients will not need or will not be able to tolerate continuous asynchronous A-V (atria-ventricular) pacing. In such patient period of normal (synchronous) pacing 401 is followed by the period of asynchronous (accelerated atrial) pacing 402 followed again by the period of synchronous pacing 403. The ventricular pacing rate 405 in this example stays the same. Switching between rates can be based on timing, patient's activity or physiologic feedbacks. For example, the pattern of therapy using electrical stimuli to generate high atrial rates can be intermittent of varying duration of accelerated atrial pacing in intervals of 10-60 minute durations occurring, for example, 3 times per day.

Commonly, in comparison to previous devices, this embodiment of the invention purposefully creates ratios of atrial to ventricular contraction higher than 1:1, such as for example in the range of 1:1 to 4:1. In addition, any previous device that allowed more that a 1:1 ratio of contraction based this relationship on sensing native atrial depolarization and deferring generation of a ventricular pacing stimulus (skipping premature ventricular beats). In contrast, in the illustrated embodiment, the higher than 1:1 rate is intentionally and controllably initiated by the implantable generator. As a result the atrial rate is increased to a rate which causes the release of sufficient endogenous naturetic hormone to result in a therapeutically beneficial increase in blood plasma levels of the hormones or increased levels in any other vascular or non-vascular space in which these hormones a found.

It is desirable to cause a therapeutic increase of blood plasma ANP and BNP via an increased endogenous release of ANP and BNP from the atria of the patient's heart. Atrial release is mediated via increase of atrial wall stress. The best embodiment of the invention known to the inventors at the time of the invention is rapid pacing of the atria that is expected to increase the rate of contractions of the atria and release ANP and BNP. The invention has been described in connection with the best mode now known to the applicant inventors. The invention is not to be limited to the disclosed embodiment. Rather, the invention covers all of various modifications and equivalent arrangements included within the spirit and scope of the appended claims.

Figure 5:
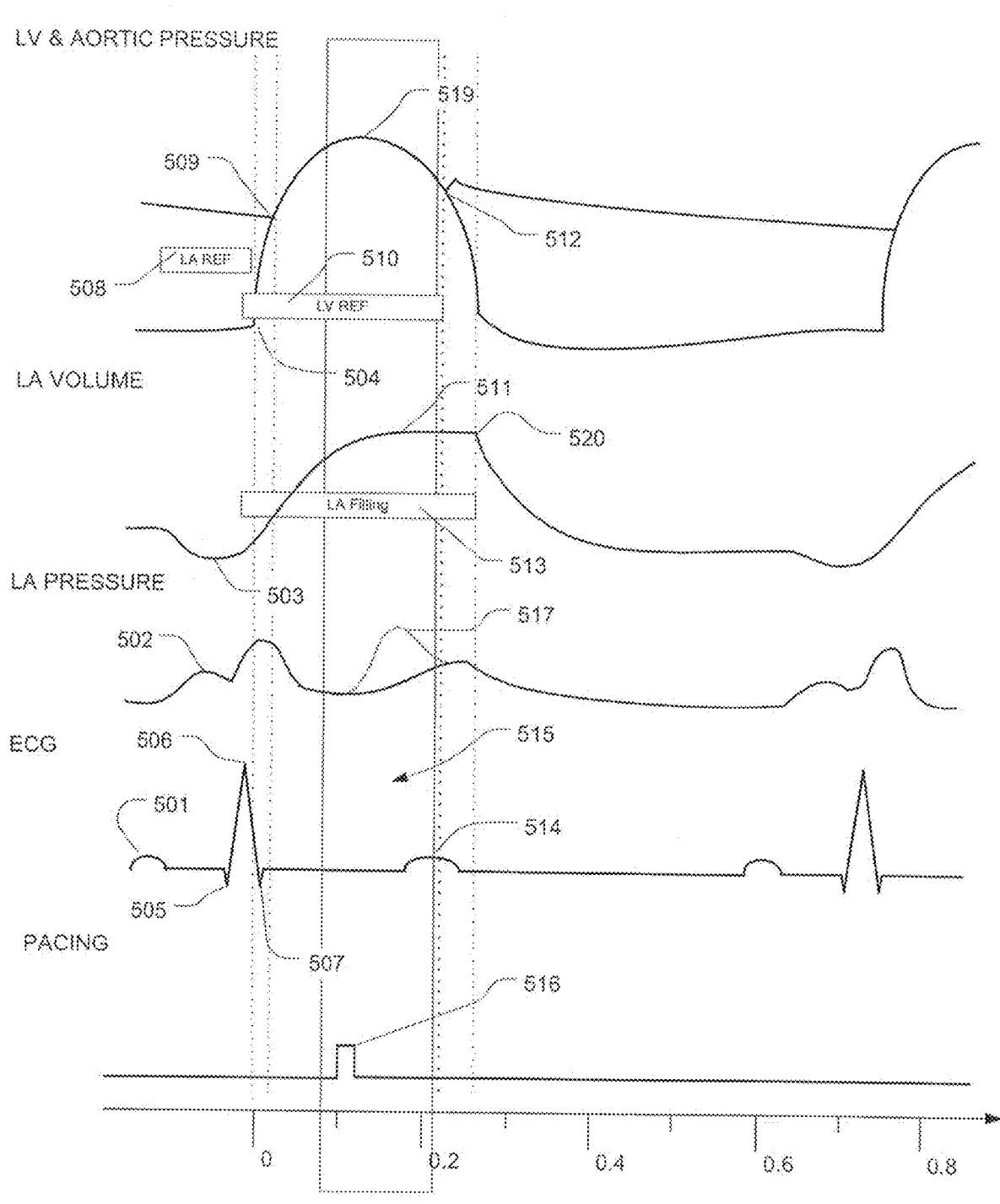
FIG. 5 illustrates timing of the refractory period pacing.

FIG. 5 illustrates the refractory period atrial pacing of the heart. The heart (See FIG. 1) has intact electric conduction including substantially normal physiologic intact A-V node conduction delay. Pacing in this embodiment is implemented by electric stimulation with an atrial lead 203 (See FIG. 2). Sensing of electric activity can be performed with the atrial lead 203 or ventricular lead 202.

Natural pacemaker or SA node of the heart initiates the Heart cycle with the P wave 501 of the ECG that corresponds to the beginning of atrial contraction. It is also the beginning of the heart systole. Atrial pressure 502 increases and atrial volume 503 decreases. This time corresponds to the beginning of the atrial refractory period 508. During this period atria can not be paced to contract.

The P wave of the ECG is followed by the Q wave 505 that signifies the beginning of the isovolumic contraction of the ventricle. Ventricular pressure 504 rise begins rapidly. In response the Tricuspid and Mitral valves of the heart close. Ventricular refractory period 510 begins. At the end of isovolumic contraction 509 Pulmonary and Aortic valves open and the ejection of blood from the ventricle begins. Ventricular pressure reaches its peak in the middle of systole 519. Atrium is passively filled with blood as it relaxes 513. Approximately by the middle of systole both heart atria are filled with blood 511 and their refractory period is over. Atria are primed for a new contraction while the ventricle is ejecting blood. A-V valves are closed. At the same time the ventricle is still refractory and will not start another contraction in response to a natural or artificial pacing stimulus. Heart waves Q 505, R 506 and S 507 are commonly used markers of the beginning of the isovolumic contraction and the beginning of ventricular ejection (S wave). All modern pacemakers are equipped with means to read and analyze the ECG that are suitable for this embodiment of the invention.

Systole ends when the aortic valve closes 512. Isovolumic relaxation of the ventricle starts. This point also corresponds to the middle of the T wave 514 of the ECG. Importantly for the invention, the middle of T wave 514 corresponds to the end of the absolute refractory period of the ventricle. At the end of the T-wave Tricuspid and Mitral valves open and the atrium volume starts to drop 520 as the blood starts to flow from the atria into ventricles to prime them for the next ventricular contraction and ejection.

For this embodiment of the invention the window of pacing opportunity 515 starts after the end of the atrial refractory period 508 and preferably but not exclusively after the atrium is filled with blood 511 and extended. During this window the atrium is primed and can be paced with a pacemaker pulse 516 that can occur at approximately the middle of systole or approximately 100-150 ms following the detected R wave 506 and/or 300 ms after P wave 501 is detected. Both P-wave and R-wave can be used by themselves or in combination to trigger pacing 516. In response to pacing 516 atrium contracts generating a pressure rise 517 that results in the desired increased stress of the atrial wall muscle, release of atrial hormones and vagal neuro activation. Significantly the window 515 overlaps the ventricular refractory period 510. Pacing atria outside of that time period is not desired since it can cause an arrhythmia and a premature ventricular beat.

As a result of the proposed therapy heart atria will beat at the rate 2:1 in relation to the heart ventricles. First physiologic atrial contraction 502 will be initiated by the natural pacemaker of the heart. Second non-physiologic atrial contraction 517 will occur during the heart systole, when the ventricle is refractory to stimulation. It may not be necessary to pace during every natural heart beat. Pacing can be applied only during part of the day or every second or third beat to give heart the needed rest and prevent of delay potential chronic dilation of the double-paced atria and potential heart failure.

Figure 6:
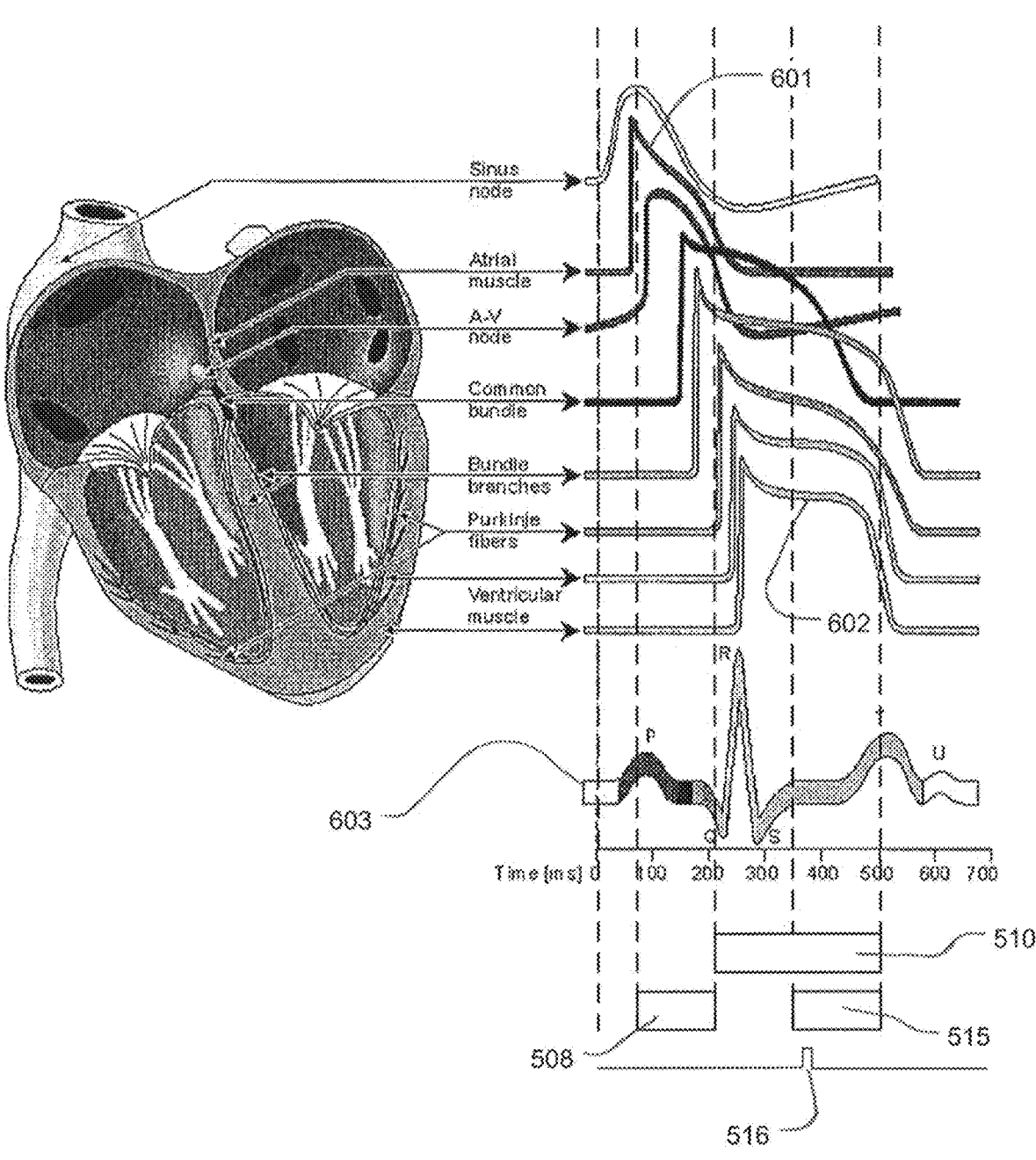
FIG. 6 illustrates an exemplary relationship between electric activity of the heart and an embodiment of a proposed pacing method.

FIG. 6 further illustrates a relationship between the electric activity of the heart and the proposed novel pacing method. Atrial refractory period corresponds to the depolarization of cells in the atrium muscle 601. Ventricular refractory period corresponds to the depolarization of cells in the muscle of the ventricle 510. Pacing 516 generates second atrial contraction during the window 515. Appropriate trigger points such as P-Q-R-S waves of the ECG 603 can be used by the embedded pacemaker software to generate the pacing spike 516 after an appropriate delay has elapsed from the selected P or R wave or both. This delay can be adjusted by the physician by reprogramming the pacemaker or automatically corrected based on the patient's heart rate. In most general terms pacing should occur after the R wave and before the T wave of the ECG 603. A delay of approximately 100-150 ms can be implemented after the R wave to allow atria to safely exit the relative refractory period and to allow atria to distend and fill with blood.

The invention has been described in connection with the best mode now known to the applicant inventors. The invention is not to be limited to the disclosed embodiment. Rather, the invention covers all of various modifications and equivalent arrangements included within the spirit and scope of the appended claims.

What is claimed is:

1. A method for treatment of heart failure, the method comprising:

artificially pacing an atrium of a heart of a patient during a period between an end of an atrial refractory period and an end of a ventricular refractory period, wherein the artificial pacing causes the atrium of the heart to contract against an already closed heart valve of the atrium that has stopped blood flow from the atrium to a ventricle associated with the atrium, such that the contraction distends a wall of the atrium with blood, and wherein the distention of the wall results in an increased secretion of atrial natriuretic peptide and/or brain natriuretic peptide, which limits vasoconstriction and/or sodium retention.

2. The method of claim 1, wherein the artificial pacing causes the atrium to contract at or after a middle of ventricular systole when the atrium is distended by passive filling with blood.

3. The method of claim 1, wherein the distention of the wall results in increased secretion of atrial natriuretic peptide in the patient to a level that overcomes detriments from reduced atrial contribution to cardiac output.

4. The method of claim 1, wherein the contraction of the atrium against the already closed heart valve of the atrium produces reverse blood flow and nonphysiologic pressure waves.

5. The method of claim 1, further comprising pacing the ventricle at a first rate, and pacing the atrium at a second rate that is faster than the first rate.

6. The method of claim 1, further comprising alternating between a first pacing period of time that comprises the atrium contracting against the already closed heart valve and a second pacing period of time that is different from the first pacing period.

7. The method of claim 6, wherein the second pacing period comprises synchronous atria-ventricular pacing.

8. The method of claim 1, wherein artificially pacing the atrium comprises cyclically: (a) applying artificially induced contractions of the atrium and (b) allowing naturally occurring contractions of the atrium.

9. The method of claim 1, wherein the artificial pacing causes the atrium to contract during heart systole, when the ventricle is refractory to stimulation.

10. The method of claim 1, wherein the artificial pacing causes the atrium to contract when the heart valve is closed by a ventricular pressure that exceeds a pressure of the atrium.

11. A method for pacing a heart of a patient suffering from heart failure, the method comprising:

delivering an excitatory stimulation to an atrium of the heart during a period between an end of an atrial refractory period and an end of a ventricular refractory period;

causing, with the excitatory stimulation, the atrium of the heart to begin contracting against a closed heart valve of the atrium after the heart valve has closed and stopped blood flow from the atrium to a ventricle associated with the atrium;

causing, with the contraction of the atrium, a pressure rise within the atrium that distends a wall of the atrium;

causing, with the distention of the wall of the atrium, stress of muscle of the wall of the atrium; and causing, with the stress of the muscle of the wall of the atrium, release of an atrial hormone that reduces vasoconstriction and/or sodium retention.

12. The method of claim 11, wherein the excitatory stimulation is delivered to the atrium at or after a middle of ventricular systole when the atrium is distended by passive filling with blood.

13. The method of claim 11, wherein causing release of the atrial hormone comprises increasing release of the atrial hormone to a level that overcomes detriments from reduced atrial contribution to cardiac output.

14. The method of claim 11, wherein causing release of the atrial hormone comprises increasing release of the atrial hormone and vasodilation to a level that offsets suboptimal performance of the heart due to reduced atrial contribution to cardiac output.

15. The method of claim 11, further comprising pacing the ventricle at a first rate, and wherein delivering the excitatory stimulation comprises pacing the atrium at a second rate that is faster than the first rate.

16. The method of claim 11, further comprising alternating between a first pacing period of time that comprises the atrium contracting against the closed heart valve of the atrium and a second pacing period of time that is different from the first pacing period.

17. The method of claim 16, wherein the second pacing period comprises synchronous atria-ventricular pacing.

18. The method of claim 11, wherein the contraction of the atrium against the closed heart valve of the atrium produces reverse blood flow and nonphysiologic pressure waves.

19. A system for treatment of heart failure, the system comprising:

a programmable implantable pacemaker connectable to at least one electrically conductive lead for connecting to a heart of a patient, wherein the pacemaker is programmed to artificially pace, through the at least one electrically conductive lead, an atrium of the heart of the patient during a period between an end of an atrial refractory period and an end of a ventricular refractory period, wherein the artificial pacing causes the atrium of the heart to contract against an already closed heart valve of the atrium that has stopped blood flow from the atrium to a ventricle associated with the atrium, such that the contraction distends a wall of the atrium with blood, and wherein the distention of the wall results in an increased secretion of atrial natriuretic peptide and/or brain natriuretic peptide, which limits vasoconstriction and/or sodium retention.

20. The system of claim 19, wherein the contraction of the atrium against the already closed heart valve of the atrium produces reverse blood flow and nonphysiologic pressure waves.

* * * * *